US008083673B2

(12) United States Patent
Rosen

(10) Patent No.: US 8,083,673 B2
(45) Date of Patent: Dec. 27, 2011

(54) EXAMINATION APPARATUS

(76) Inventor: Howard Steven Rosen, Denver, CO (US)

( * ) Notice: Subject to any disclaimer, the term of this patent is extended or adjusted under 35 U.S.C. 154(b) by 854 days.

(21) Appl. No.: 12/146,426

(22) Filed: Jun. 25, 2008

(65) Prior Publication Data

US 2009/0326331 A1 Dec. 31, 2009

(51) Int. Cl.
*A61B 1/32* (2006.01)
(52) U.S. Cl. ......... 600/224; 600/210; 600/219; 600/220
(58) Field of Classification Search .................. 600/210, 600/214, 215, 219–225
See application file for complete search history.

(56) References Cited

U.S. PATENT DOCUMENTS

| | | |
|---|---|---|
| 3,332,414 A | 7/1967 | Gasper |
| 3,575,163 A | 4/1971 | Gasper |
| 3,815,585 A | 6/1974 | Fiore |
| 3,890,961 A | 6/1975 | Moore et al. |
| 4,597,382 A * | 7/1986 | Perez, Jr. .................. 600/203 |
| 5,377,667 A | 1/1995 | Patton et al. |
| 5,505,690 A | 4/1996 | Patton et al. |
| 5,509,893 A | 4/1996 | Pracas |
| 5,868,668 A | 2/1999 | Weiss |
| 5,997,474 A | 12/1999 | Batchelor |
| 6,004,265 A | 12/1999 | Hsu et al. |
| 6,024,696 A | 2/2000 | Hoftman et al. |
| 6,048,308 A | 4/2000 | Strong |
| 6,280,379 B1 | 8/2001 | Resnick |
| 6,354,995 B1 | 3/2002 | Hoftman et al. |
| 6,364,832 B1 | 4/2002 | Propp |
| 6,379,299 B1 | 4/2002 | Borodulin et al. |
| 6,416,466 B1 | 7/2002 | Hsiao |
| 6,416,467 B1 | 7/2002 | McMillin et al. |
| 6,432,048 B1 | 8/2002 | Francois |
| 6,436,033 B2 | 8/2002 | Tan |
| 6,569,091 B2 | 5/2003 | Diokno et al. |
| 6,669,654 B2 | 12/2003 | Diokno et al. |

(Continued)

FOREIGN PATENT DOCUMENTS

WO WO 98/11818 A1 3/1998

OTHER PUBLICATIONS

Quinn, M.J., An Illumunated Vaginal Speculum, American Journal of Obstetrics and Gynaecology, Jan. 1999, pp. 33-34 (United States).

(Continued)

*Primary Examiner* — Thomas C. Barrett
*Assistant Examiner* — Michael T Schaper
(74) *Attorney, Agent, or Firm* — Roger A. Jackson

(57) ABSTRACT

An apparatus and method for an examination apparatus that includes a manually movable structure having a first movement from a free state to a compressed state and a second reversing movement from the compressed state to the free state. Also included is a plurality of fingers that are disposed adjacent to the structure. The fingers having a stowed state and an open state, the stowed state having a nested relationship between the fingers to reduce a silhouette profile size. In moving from the stowed state to the open state of the plurality of fingers requires a selected sequential movement of each the fingers to proceed from the nested relationship to the open state that is accommodated by an assemblage for moving the fingers sequentially utilizing the manually operated structure, wherein the fingers are moved from the stowed state to the open state and reversed manually.

3 Claims, 26 Drawing Sheets

U.S. PATENT DOCUMENTS

| | | |
|---|---|---|
| 6,712,761 B2 | 3/2004 | Borodulin et al. |
| 6,869,398 B2 | 3/2005 | Obenchain et al. |
| 7,060,029 B1 | 6/2006 | Hajianpour |
| 7,070,561 B1 | 7/2006 | Ansari |
| 7,141,015 B2 | 11/2006 | Ruane |
| 7,311,663 B2 | 12/2007 | Marcotte |
| 7,344,495 B2 | 3/2008 | Ravikumar et al. |
| 7,371,212 B2 | 5/2008 | Klaassen |
| 7,481,766 B2 | 1/2009 | Lee et al. |
| 7,658,712 B2 | 2/2010 | Klaassen et al. |
| 7,780,594 B2 | 8/2010 | Hutton |
| 2005/0080320 A1 | 4/2005 | Lee et al. |
| 2007/0156026 A1 | 7/2007 | Frasier et al. |
| 2007/0208227 A1 | 9/2007 | Smith et al. |
| 2009/0069635 A1 | 3/2009 | Gephart et al. |
| 2009/0259109 A1 | 10/2009 | Bucefari et al. |
| 2009/0275803 A1 | 11/2009 | Krauter et al. |

OTHER PUBLICATIONS

Greenberg, James A., Journal of the Society of Laparoendoscopic Surgeons, Jan. 1, 2006, pp. 129-130 (United States).

* cited by examiner

EXAMINATION APPARATUS

TECHNICAL FIELD

The present invention generally relates to an apparatus for examining a resilient cavity. More particularly, the present invention is an apparatus that manually penetrates into and expands the resilient cavity a manually selected amount for examination with the apparatus having the ability to be selectively manually retracted and manually withdrawn from the cavity.

BACKGROUND OF INVENTION

Apparatus for resilient cavity inspection or examination have been well-documented in the prior art, especially in the area of human medical apparatus for examination of body cavities. Looking in particular at surgical retractors that can also be termed speculum apparatus that are employed for the use of gynecological examinations the following general analysis of the speculum arts is given. Speculum's generally have blades shaped as extension fingers that are movable between a closed state and an open state, wherein the blades are typically formed as an elongated spoon shaped extension finger with one finger typically nesting within another finger in the closed state for a more streamlined penetration for insertion into the body cavity. Once the speculum is inserted into the body cavity, the speculum is then manually moved from the closed state to the open state, resulting in the subsequent spreading of some or all of the fingers to physically expand the body cavity for examination. As is the typical case for the majority of prior art speculums, the speculum fingers are pivotally connected at one end and are free on the other hand in a cantilevered type configuration.

The primary objective in the speculum's use is to allow the service provider examining the patient's body cavity or as typically the case a vagina, for the service provider to have a full and clear of view as possible of the area disposed within the cavity while also having as free and open access as possible around and through the speculum itself with the speculum acting to obfuscate or block the service provider's view or access in a minimal manner. In focusing upon the speculums pivotally connected fingers there exists an undesirable limitation in the service provider's viewing field of the body cavity and that the pivotal connection is fixed in its physical size adjacent to the pivotal axis of movement and does not allow for an increased field of vision as the fingers are manually expanded outward, i.e. in going from the closed state to the open state. In fact there could be some additional restriction of the service provider's view and access to the body cavity when the speculum fingers are moved from the closed state to the open state due to the fingers possibly pivoting inward on their end opposite of their cantilever end.

Focusing in particular on the vagina speculum which in the past has been primarily used to visualize the cervix and vagina walls in addition to gaining access to the uterus. As previously mentioned there is non-optimal limitation on a portion of the prior art speculums as to the pivotal connection of the fingers restricting the service provider's view and access to the interior of the vagina and in particular the vaginal wall structure. The vaginal wall structure poses a particular problem for service provider examination in that the vaginal wall structure is comprised of soft, somewhat unsupported, and fatty tissue that is difficult to control in the speculum structurally supporting the vaginal wall apart from itself somewhat resembling soft bread dough. This results in the speculum fingers opening up against the vagina walls in going from the closed state to the open state wherein the vaginal wall tissue surrounding the finger tends to collapse around the finger due to its lack of support stiffness resulting in a further hampering of the service provider's view of the inside wall vagina. This problem of the vaginal wall collapsing around the finger is especially prevalent if the patient is overweight, is older in age, or has had children through the vaginal tract.

Furthermore, as the vagina wall collapses around the finger, the reaction may be that the examining service provider is motivated to open the fingers to an even greater distance apart to gain a better visual of the cervix. However, this may be a self defeating effort as the previously mentioned problem of the vagina wall collapsing around the finger becomes even more acute as the figures are moved a further distance part, thus there is very little to be gained upon moving the speculum fingers further part to gain a better visual orientation of the vagina and cervix. Further, another problem of course is patient comfort, as the fingers are expanded further and further apart patient discomfort increases due to a number of issues such as the physical outward force as against the stretching of the introitus, in addition to the sliding and scraping action of the finger against the vagina wall also causing patient discomfort, and the subsequent risk of vagina wall pinching when the fingers are retracted into their closed state or nested position in preparation for extraction or withdrawing of the speculum from the vagina.

A number of prior art solutions have been proposed dealing with the different methods of which vagina walls are expanded for visual contact and physical access by the service provider while at the same time allowing for a minimal amount of blockage for the service provider to potentially use instruments in the vagina while at the same time being able to visualize the nature of the examination or therapeutic procedure that the service provider is performing. The majority of the early use speculums had pivotally connected fingers, typically having just two fingers that simply spread apart from the depression of a thumb lever which usually included a mechanism to lock the fingers in a particular pivotal position state in a selectable manner by the service provider. Although simple in design and easy to use, being somewhat similar to spreader pliers tools, the early use speculum having only two fingers and a pivotal connection at one end had limited ability to enhance visual contact of the service provider with the vagina walls due to the vagina with wall collapse as a position intermediate to the spread apart portions of the fingers, i.e. in the open state as previously described.

In addition, in the early use speculums due to the nature of the larger circumferential distance of each finger resulting in a larger area of the finger itself undesirably covered up larger portions of the vagina wall thus impeding visual and physical access of the service provider to the vagina wall. Plus, the early use speculum undesirably inflicting additional discomfort upon the patient as previously described due to the large amount of separating movement of the fingers to each other in going from the closed state to the open state. More refined solutions included speculum apparatus that used more than two fingers that could be opened in an iris aperture type of movement, wherein the fingers are moved outwardly in typically a spiraling motion. However, the iris type of speculum had two major drawbacks; the first drawback being that when each individual finger opened it moved through a circumferential type of arc and caused a relative sliding motion as against the vagina wall causing patient discomfort through a pinching of the vaginal wall tissue with the second drawback of the complex mechanism with which to move the fingers. Thus this circumferential arc finger movement of the iris type speculum can be compared to the pivotal speculum finger arrangement wherein the pivotal finger moves outwardly without circumferential arc movement, thus resulting in less discomfort for the patient.

The complex mechanism for the iris type of speculum further causes problems from potentially interfering with the service providers view and access to the vagina as a speculum should accommodate an open field of view and physical access along a longitudinal axis parallel to the fingers in the service provider being positioned at the non-inserting end of the speculum. Continuing, in looking to the pivotal type of speculums that use more than two fingers, wherein the undesirable circumferential arc movement is eliminated, again the problem of having three or more fingers having to have a complex mechanism usually located at the position where the service provider needs the maximum access and field of view for the vagina is a drawback.

Although the multitude of speculum fingers being more than two fingers pivoting outward without circumferential arc movement for less patient discomfort as previously described, does positively provide for less distance between each finger in the open state resulting in a reduced span of distance for the vaginal wall to droop between fingers thus giving the service provider greater access and visualization of the vagina, in addition to the reduction in patient discomfort as the fingers do not need to be as far apart from one another as compared to the two finger speculum. However, having more than two fingers adds complexity to the mechanism for moving the fingers in-between the closed state and the open state which adds size and weight to the speculum on the end opposing the cantilevered finger portions. Thus a speculum having more than two fingers in generally beneficial by helping reduce the occurrence of the vagina wall collapsing from around the finger and the resulting loss of view and access for the service provider and for reducing patient discomfort. Further, it should be noted that as these speculum apparatus are a manually hand held instrument; size and weight are considerations that should be desirably minimized.

Continuing, in looking at some specific examples in the prior art starting with the typical early use type speculum, in U.S. Pat. No. 5,997,474 to Batchelor disclosed is a vaginal speculum comprising two arms hinged with one another at a point along their length and forming a pair of jaws on one side of the hinge point and a pair of handles on the opposite side of the hinge point such that the jaws can be separated by squeezing together the handles. An elongated locking member in Batchelor is pivotally mounted to one handle, with the locking member having enough friction to hold it in position against its weight, reference column 1, lines 29-33 and lines 43-46. Batchelor had added the features of an elongated handle for the entire hand of the service provider to be able to grip the speculum as opposed to the thumb lever that had been previously employed on earlier speculums to give more opening force to the arms and including a new design locking member to hold the arms in a selected position apart.

Similar to Batchelor in design for the spreading apart fingers and the pivotal handle arrangement, in looking at U.S. Pat. No. 6,416,466 to Hsiao disclosed is a vaginal speculum that is made of metal or plastic including an upper and a lower jaw forming a concave profile. In Hsiao, the end part of the jaw opposite from the insertion end of the lower jaw is extended, whereby a patient's secretion can be exhausted or channeled along the extended end part for avoiding contact with the service provider's hands, reference column 1, lines 43-48 and lines 56-60. In addition to the new secretion irrigation channel, Hsiao has a plurality of buckling members used for locking the jaws into a selected position. In addition, in being somewhat similar to Batchelor and Hsiao, in having a veterinary application speculum, in Ukraine patent number UA 9,393 U to Tsymerman et al. disclosed is a vaginal speculum for examining females of large animals equipped with reflector and electric lamp connected with a power supply. In Tsymerman et al., the movable handle of the upper branch is attached with the fixed handle of the lower branch by the retainer screw with two nuts for the locking mechanism of the spreadable fingers including the addition of a light adjacent to the upper finger.

Continuing further, in an example of an iris type of expanding speculum, in U.S. Pat. No. 6,354,995 to Hoftman et al. disclosed is a rotational lateral expander apparatus having multiple blades. As a typical example, four blades in Hoftman et al., are arranged so that their forcing planes are facially parallel to each other in a closed or nested position, reference column 1, lines 51-57. In Hoftman et al., specifically referring to FIGS. 1 to 5, it can be seen that the blades must have a sliding motion as against the vaginal wall structure which can lead to patient discomfort as the vaginal wall structure can be pulled, compressed, and pinched as the blades move from their closed state to their open state and in returning from the open state to the closed state. Hoftman et al., has the feature of the translation of forceps type movement into the iris type movement through a mechanism to effectuate the blades going from the closed state to the open state in the rotating base plate that connects to a lateral expansion of the blades that open laterally and rotationally simultaneously.

As an example of a pivotal blade speculum having more than two blades in looking at U.S. Pat. No. 6,280,379 to Resnick disclosed is a speculum using small "bullet shaped" diameter tips on the distal ends of the blades which may be comprised of plastic, or coated metal to reduce friction, or reduce the "cold" sensation of the patient, reference column 2, lines 55-67. The Resnick speculum also has four blades to expand the vaginal walls, with three of the blades actually having expanding/contracting movement in somewhat of a mechanically open manner, having a degree of free play as between the blades and the handle structure. Due to the larger and somewhat complex mechanism in Resnick required to expand and retract three blades from a pistol grip handle, say as compared to the simple and small mechanism in Batchelor for example, the Resnick speculum is slightly heavy and cumbersome, being an undesirable feature of a manually hand held instrument. Further to this in Resnick, the additional hand squeezing force required to move three blades as compared to the prior art moving a single blade, again as in Batchelor, adds to the difficulty in using the Resnick speculum. In Resnick this would be considered a design requirement as a greater mechanical advantage mechanism, as between the compressible handgrip and blades, has been employed to a limited extent with the blade hook end 16, see FIG. 1 (closed state) and FIG. 5 (open state), i.e. the travelling ring 10 moving further from the blade pivot point sleeve 18 that is upon the stationary ring 8, resulting in a greater moment arm, which is a positive. However, Resnick does not really take full advantage of this moment arm increase due to only a portion of the travelling ring 10 force taking advantage to the increased moment arm as the distance between the travelling ring 10 and the blade pivot point sleeve 18 upon the stationary ring 8 remains substantially constant in an axis perpendicular to the force vector on the travelling ring 10 when moving the blades from the closed state to the open state.

A further example of a four blade speculum that addresses the mechanical complexity issue for the three to four blade movement from the handgrip, is in U.S. Pat. No. 7,060,029

B1 to Hajianpour, that discloses a basically conventional early use type pivotal two blade speculum, i.e. designed for contacting the anterior and posterior vaginal wall portions being similar to Batchelor, with having the addition of attachable/removable opposing lateral blades, wherein the lateral blades are attached and removed when the conventional portion of the speculum is in an open state by compressing as against the anterior and posterior vaginal walls. Thus Hajianpour attempts to have the advantage of the four blade speculum without the complexity, size, and weight of three or four blades moving together from a handle grip, however, the compromise being disadvantage of the loose lateral blade pieces that have to be manually positioned and attached and removed each time an examination is performed. Close to Hajianpour in U.S. Pat. No. 6,146,467 B1 to McMillian et al., is another speculum with a conventional pivotally connected two finger design that "adds in" two additional lateral blades that have their own independent thumb screw adjustment that is not connected to the primary anterior and posterior fingers.

Another example of a four blade speculum is in United States patent number U.S. Pat. No. 6,869,398 B2 to Obenchain et al., that discloses the use of an extensive mechanism for the selectable positioning of the four blades, even though Obenchain et al., has a very elaborate blade positioning arrangement, the size and weight dictate that additional support is required as the speculum cannot be supported by the body cavity or the examining service provider's hand as evidenced by the desired stabilizing arm 40 in FIG. 1. A further example in the four dilator finger area is disclosed in U.S. Pat. No. 6,436,033 B2 to Tan that is somewhat similar to Resnick except that the pivotal actuator is disposed between the finger pivot point and the free cantilever end of the finger that is inserted into the vagina, however, only being for the third and fourth blades, reference fingers 14a and 14b. In Tan, the speculum basically starts with a conventional pivotal two blade arrangement like Batchelor and then adds the third and fourth fingers that have a subsequent pivotal contact after the anterior and posterior fingers have started to open. A drawback of Tan is that there is no real mechanical advantage in the design opening mechanism that could accommodate the additional opening force required when the examining service provider in squeezing the handle encounters the opening force of four fingers from two fingers.

An even further example in the four blade speculum area, in U.S. Pat. No. 5,377,667 and its continuation follow-on application in U.S. Pat. No. 5,505,690 both to Patton et al., disclosed is a speculum that utilizes a slider plate that acts as collet in moving parallel to the speculum finger longitudinal axis, wherein the slider plate is operable to open and close the fingers by movement along the finger longitudinal axis. In Patton et al., although the slider does accomplish its purpose in opening and closing the fingers desirably, however, the slider plate adds considerable bulk and weight to the speculum opposite of the finger cantilever ends being undesirable from a service provider's standpoint plus the attendant problem of obscuring the service provider's vision and instrument access through the speculum center that is adjacent to the finger pivotal end portions opposite of the finger cantilever ends, see in particular FIGS. 6, 7, and 8.

What is needed is an examination apparatus or more particularly a speculum that does preferably utilize more than two fingers to reduce, in the finger open state, the finger to finger span distance that allows the lax vaginal wall tissue to prolapse while the speculum is inserted into the introitus of the vagina and subsequently moved to the open state of the fingers. Also, the desirable speculum would at the same time provide the examining service provider the maximum field of view through the proximal portion of the speculum being the non-insertion end of the apparatus, plus the included feature that also equates to allowing for other instruments to be used in this field of view access area. Further, the desired speculum would have a mechanism to accommodate the kinematics from the actuation structure or handle to the finger movement that would employ a greater mechanical advantage than what has been taught by the prior art for enhancing the operating experience of the examining service provider in requiring less hand grip strength as a greater number of fingers, being more than two fingers that ends up resulting in less hand fatigue for the service provider for multiple examinations that are performed in the course of the day. In addition, the entire apparatus would be of a minimal size and weight which is always a welcome feature in a hand held manually actuated speculum apparatus. Continuing, the speculum would be operable to help minimize patient discomfort by the finger having little sliding type movement as against the vaginal wall structure and having to open the fingers a minimal amount for the examining service provider to have sufficient visual and instrument access, while minimizing vaginal wall structure prolapse between the fingers in their open state, that results in maximizing the visual and instrument access to the vagina from the examining service provider through the speculum.

The vaginal wall prolapse issue is primarily due to lax vaginal wall tissue tone which is fairly common and is most typically associated with a woman having natural childbirth through the vaginal tract, or elderly women, or obese woman. Thus currently, with use of the prior art two blade or two finger speculum due to the aforementioned lax vaginal tone, the service provider typically has to open the fingers further apart to have an adequate view, with this further opening or spreading of the speculum fingers causing the patient a higher level of discomfort due to speculum finger pressure as against the bladder and/or urethra. Thus, the desirability of having more than two speculum fingers in a minimally sized and weighted speculum that could facilitate easy one-handed operation by the service provider would be substantially optimal by allowing the service provider to use their other hand for viewing lights, instruments, and the like. Further, the desirable speculum would have as previously mentioned the degree of mechanical advantage in the hand grip to blade movement mechanism that facilitates the opening of greater than two fingers without the need for excessive grip compression strength on the part of the using service provider. Other desirable features of the speculum would include; non-vaginal wall tissue pinching fingers, minimal-heat transfer fingers-to reduce the "cold" sensation for the patient, or minimal electrical conductance fingers for performing electro-surgical procedures, and further a possible light source for viewing the vaginal cavity with the speculum inserted into the vagina and in the open state, in addition to a fluid communication medium to facilitate adding or removing fluids from the vagina.

SUMMARY OF INVENTION

Broadly, the present invention is an examination apparatus that includes a manually movable structure having a first selective movement from a free state to a compressed state and a second selective movement, being a return movement from the compressed state to the free state. Also included in the examination apparatus is a plurality of fingers that are disposed adjacent to the structure. The fingers having a stowed state and an open state, the stowed state resulting in a nested relationship between the fingers to reduce a silhouette of a leading edge profile of the plurality of fingers in the stowed state. With the open state of the plurality of fingers requiring a selected sequential movement of each the fingers to proceed from the nested and stowed state relationship to the open state. Further included in the examination apparatus is an assemblage for moving the fingers utilizing the structure wherein the fingers are moved from the stowed state to said open state. Wherein, the assemblage for moving accommodates the selected sequential movement in proceeding from the stowed state to the open state and reversing the sequential movement in proceeding from the open state to the stowed state for the plurality of fingers.

These and other objects of the present invention will become more readily appreciated and understood from a consideration of the following detailed description of the exemplary embodiment(s) of the present invention when taken together with the accompanying drawings, in which;

REFERENCE NUMBERS IN DRAWINGS

Figure 1:
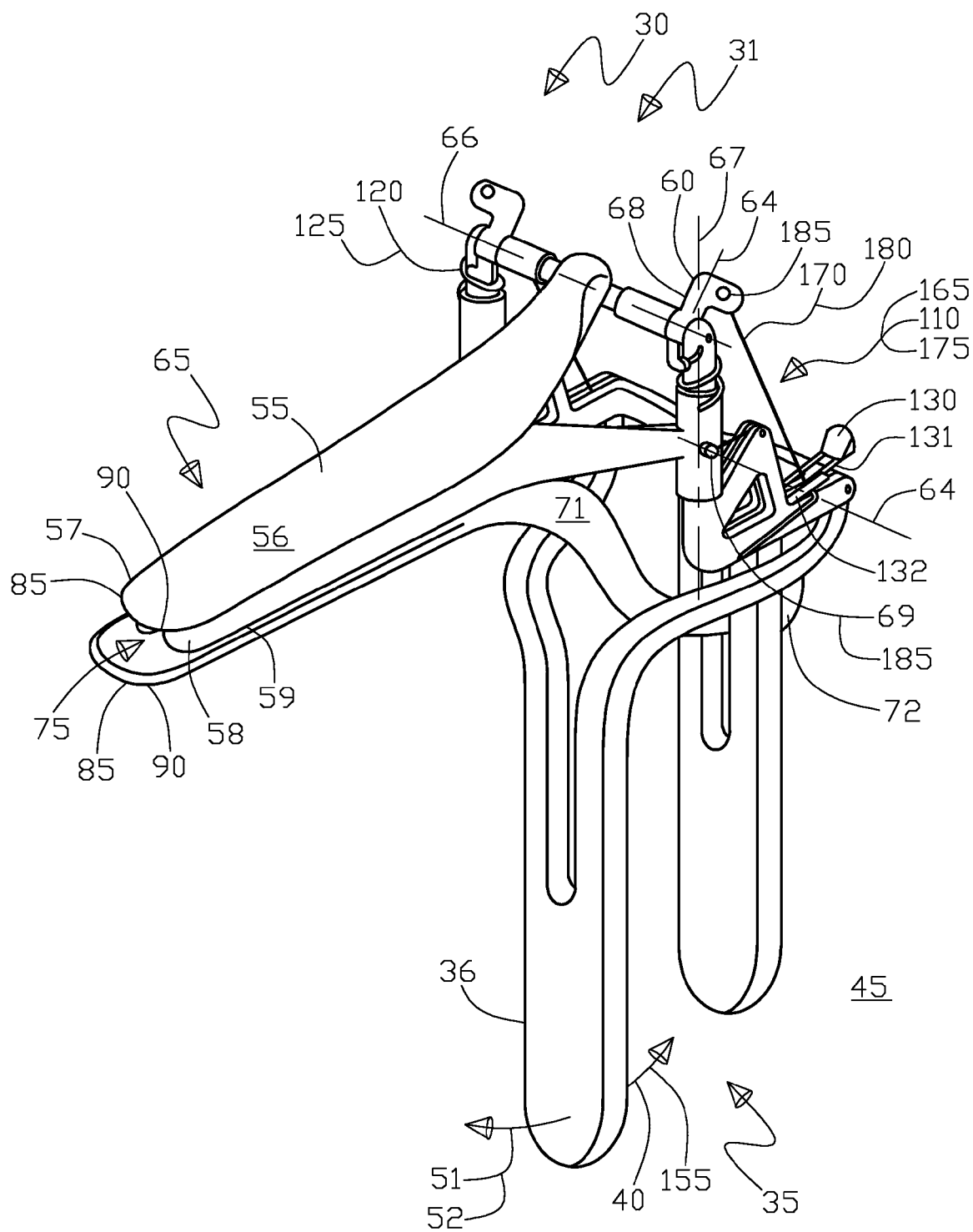
FIG. 1 shows a perspective view of the examination apparatus including the flexible elements with the fingers in the stowed state and the structure in the free state.

30 Examination apparatus
31 Examination apparatus embodiment with flexible elements 170
32 Examination apparatus embodiment with linkages 210
35 Manually movable structure
36 Movable portion of the structure 35
40 First selective movement of structure 35
45 Free state of the structure 35
50 Compressed state of the structure 35
51 Second selective movement of the structure 35
52 Return movement from the compressed state 50 to the free state 45
55 Plurality of fingers
56 First finger
57 Profile of the first finger 56
58 Second finger
59 Sizing and configuring of second finger 58 to be disposed within a profile 57 of the first finger 56
60 Pivotal moment arm of each of the fingers 55
61 Dynamic length change of the moment arm 60
62 Selectably vary moment arm 60 length
63 Initial selected moment arm 60 length
64 Axis of pivotal moment arm 60
65 Stowed state of the fingers 55
66 Pivotal axis of the first finger 56
67 Pivotal axis of the second finger 58
68 Moment arm of the first finger 56
69 Moment arm of the second finger 58
70 Open state of the fingers 55
71 Adjustable finger
72 Means for adjusting finger 71
75 Nested relationship of the fingers 55 in the stowed state 65
80 Un-nested relationship of fingers 55
85 Leading edge profile of the fingers 55 in the nested relationship 75
90 Silhouette of leading edge profile 85
95 Sequential movement of the fingers 55
100 Initial movement by a first finger 56 of selected sequential movement 95
105 Further sequential movement by the second finger 58 of selected sequential movement 95
110 Means for moving the fingers 55 from the stowed state 65 to the open state 70
115 Sizing and configuring of the means 110 for sequential movement 95
120 Means for urging the second finger 58 into the stowed state 65
121 Movement for means 120
125 Spring for means 120 on the examination apparatus embodiment 31
126 Spring for means 120 on the examination apparatus embodiment 32
130 Lockable element that selectably holds the fingers 55 at a position between the
stowed state 65 and the open state 70
131 Flexible wire rod
132 Toothed rack for removably engaging the flexible wire rod 131
133 Thumb nut
134 Threaded rod for threadably engaging thumb nut 133
135 Means for fluid communication adjacent to the fingers 55
140 Means for light communication adjacent to the fingers 55
145 Increasing mechanical advantage in the means 110 when moving the fingers 55 from the stowed state 65 to the open state 70
150 Opening force of fingers 55 from means 110 or mechanism 165 with the force 150 increasing on the fingers 55 from the stowed state 65 to the open state 70
151 Arc type movement of moment arm 60
155 Fixed manual substantially constant force on the structure 35 in proceeding from the stowed state 65 to the open state 70
160 Selectable increasing mechanical advantage 145
165 Mechanism for moving the fingers 55 from the stowed state 65 to the open state 70
170 Plurality of flexible elements in mechanism 165
171 Axis for the flexible elements 170
175 Communication of movement from the movable structure 35 to the fingers 55 that incorporates the selected sequential movement 95 in the mechanism 165
180 Cables for the flexible elements 170
181 Length of each flexible element 170
182 Selectable length 181 adjustment for each flexible element 170
183 Cable nut for cable 180
184 Threaded portion of cable 180 that threadably engages the cable nut 183
185 Adjacent position of the cable 180 to the pivotal moment arm 60 of each of the fingers 55
186 Movement lengthwise along axis parallel to path of flexible element 170
190 Opposing portion of the cable 180 to the movable portion 36 of the structure 35
195 Sizing and configuring of the mechanism 165 for the fingers 55 to have increasing mechanical advantage in the changing moment arm 60 dynamic length 61 in the fingers 55 proceeding from the stowed state 65 to the open state 70
200 Selectable device to vary 62 the pivotal moment arm 60 in length from an initial selected moment arm length 63
201 Nut for moment arm 60
202 Lock nut for moment arm 60
203 Threaded portion of moment arm 60 for threadably engaging nut 201 and nut 202
205 Assemblage for moving the fingers 55 from the stowed state 65 to the open state 70
210 Plurality of linkages in assemblage 205
211 Pivotal connection of linkage 210 to pivotal moment arm 60
215 Communication of movement from the movable structure 35 to the fingers 55 that incorporates the selected sequential movement 95 in the assemblage 205
220 Substantially rigid extension of the linkages 210
225 Adjacent position of the extension 220 to the pivotal moment arm 60 of each of the fingers 55
230 Opposing portion of the extension 220 adjacent to the movable portion 36 of the structure 35
235 Sizing and configuring of the assemblage 205 for the fingers 55 to have increasing mechanical advantage in the changing moment arm 60 dynamic length 61 in the fingers 55 proceeding from the stowed state 65 to the open state 70
240 Creature or patient
245 Examination body cavity of creature 240 or patient 240
250 Service provider using the examination apparatus 30, 31, or 32
255 Retention element
260 Field of vision

DETAILED DESCRIPTION

Figure 2:
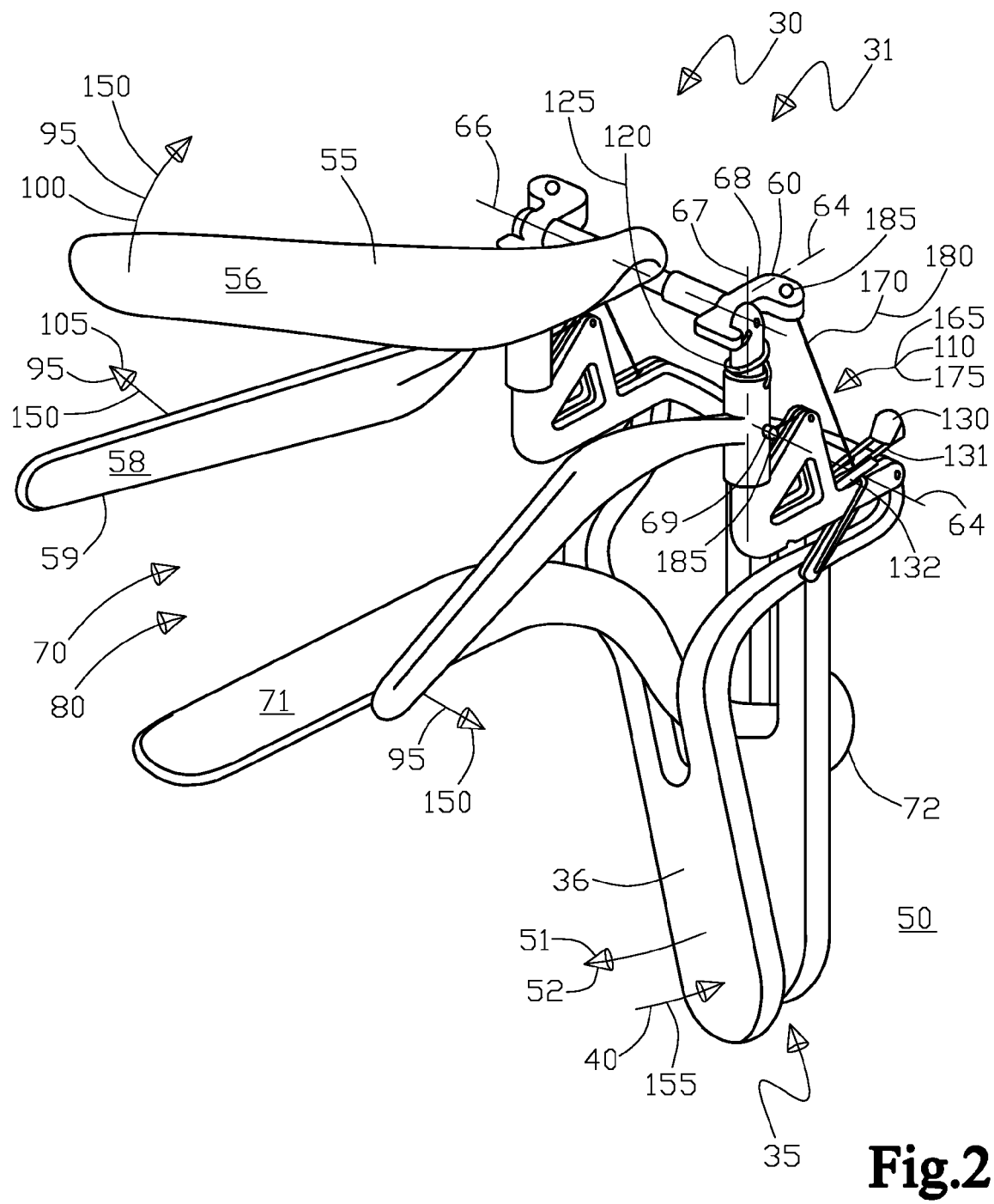
FIG. 2 shows a perspective view of the examination apparatus including the flexible elements with the fingers in the open state and the structure in the compressed state.
Figure 3:
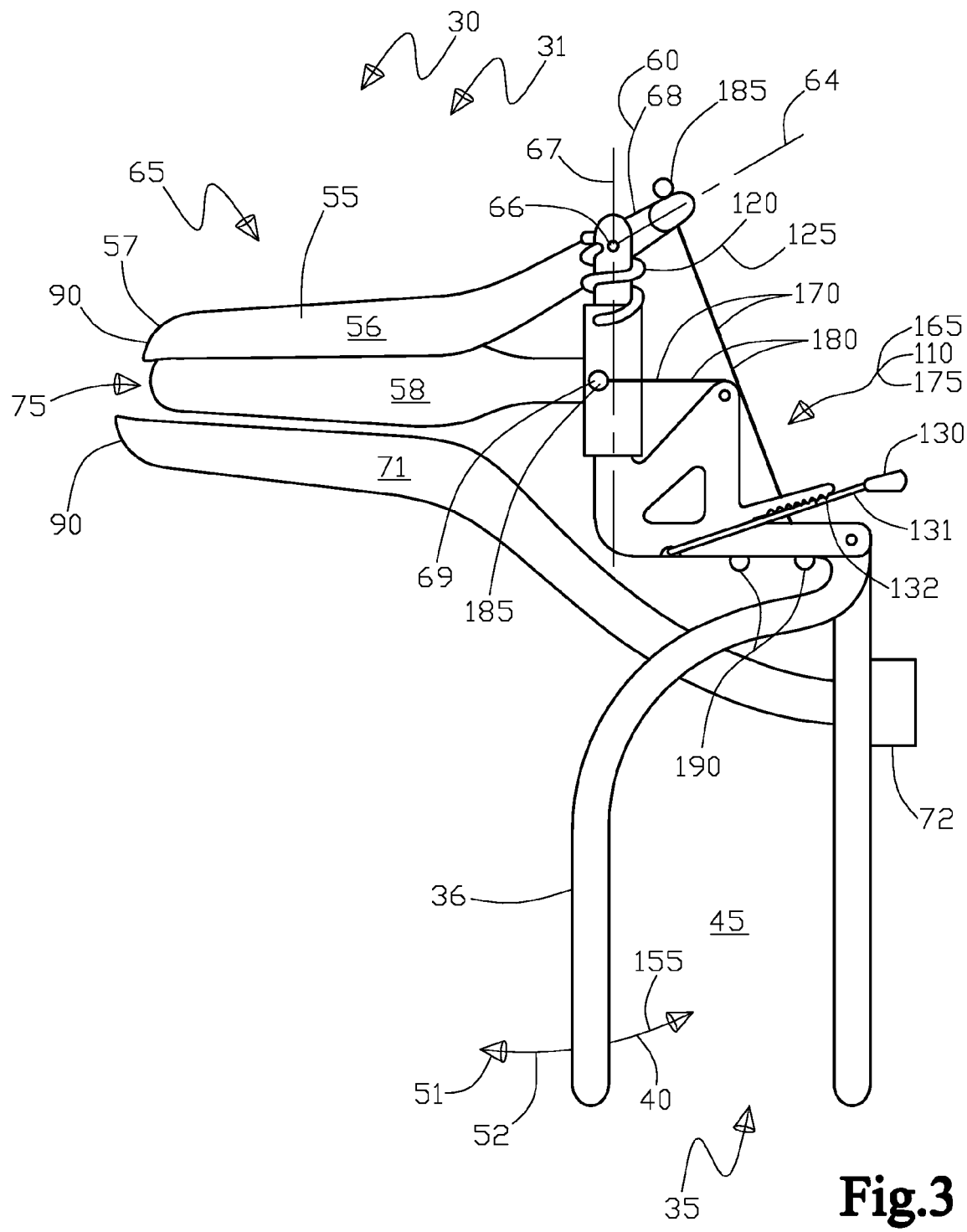
FIG. 3 shows a side elevation view of the examination apparatus including the flexible elements with the fingers in the stowed state and the structure in the free state.
Figure 4:
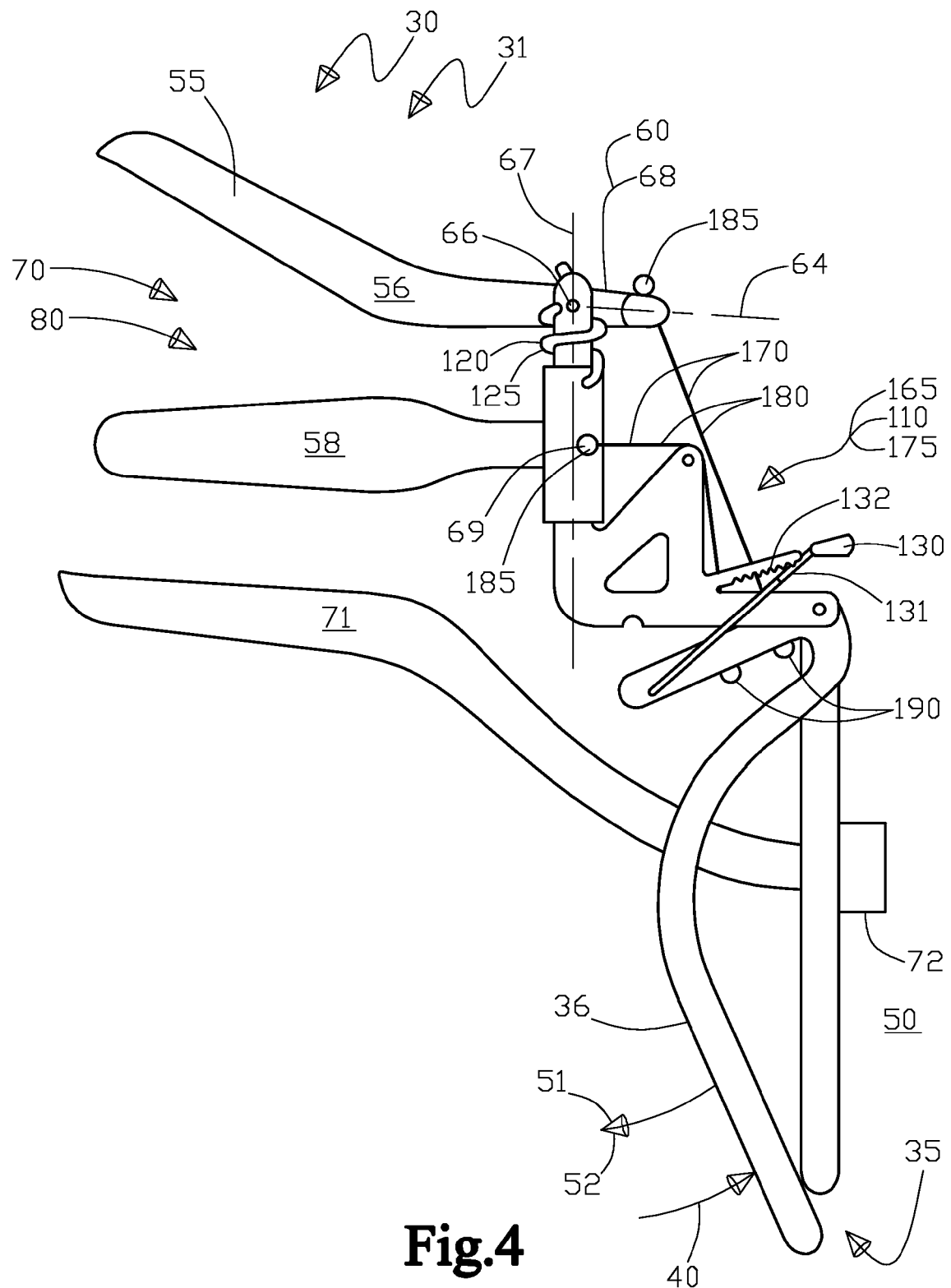
FIG. 4 shows a side elevation view of the examination apparatus including the flexible elements with the fingers in the open state and the structure in the compressed state.
Figure 5:
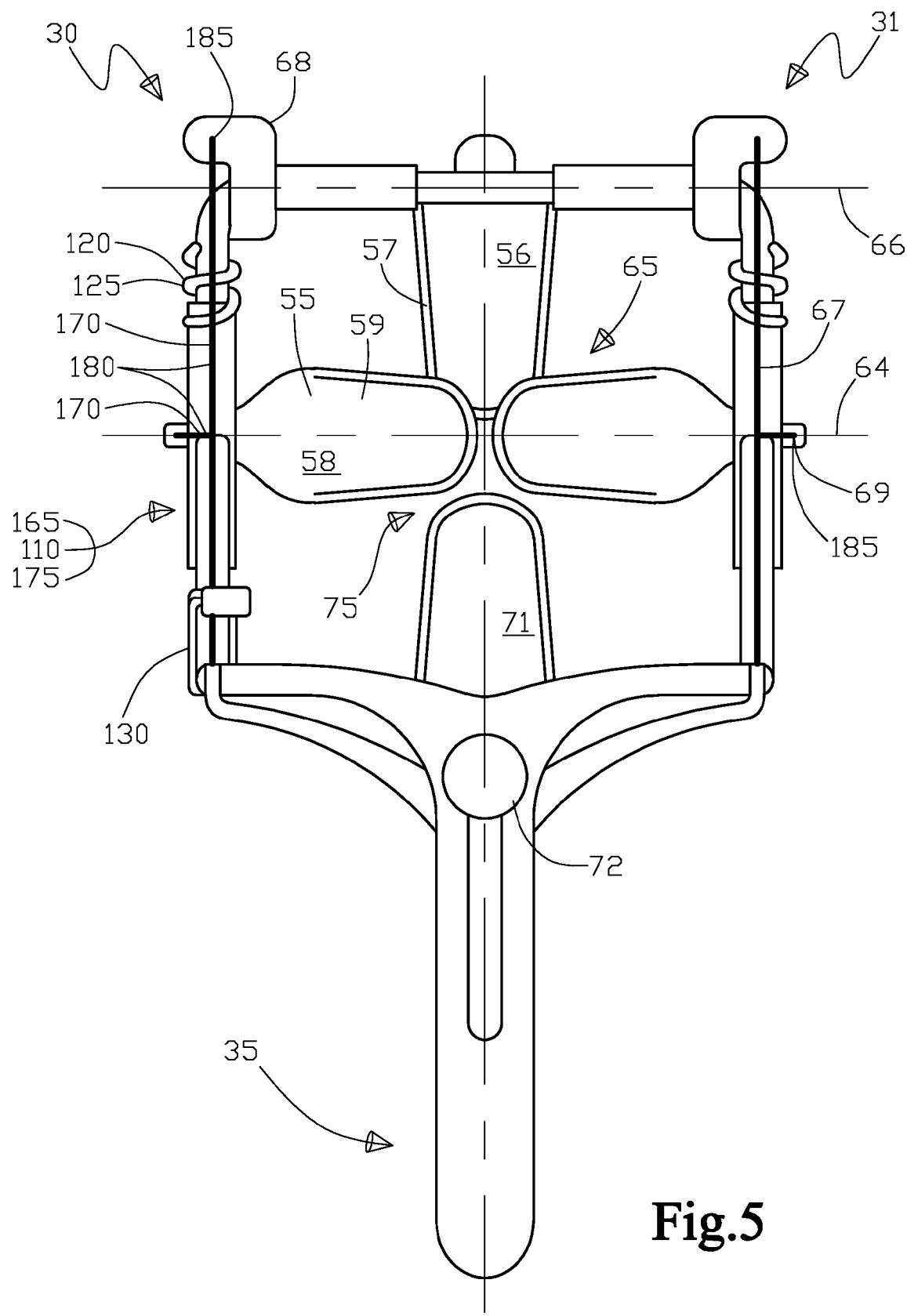
FIG. 5 shows a service provider end view of the examination apparatus including the flexible elements with the fingers in the stowed state and the structure in the free state.
Figure 6:
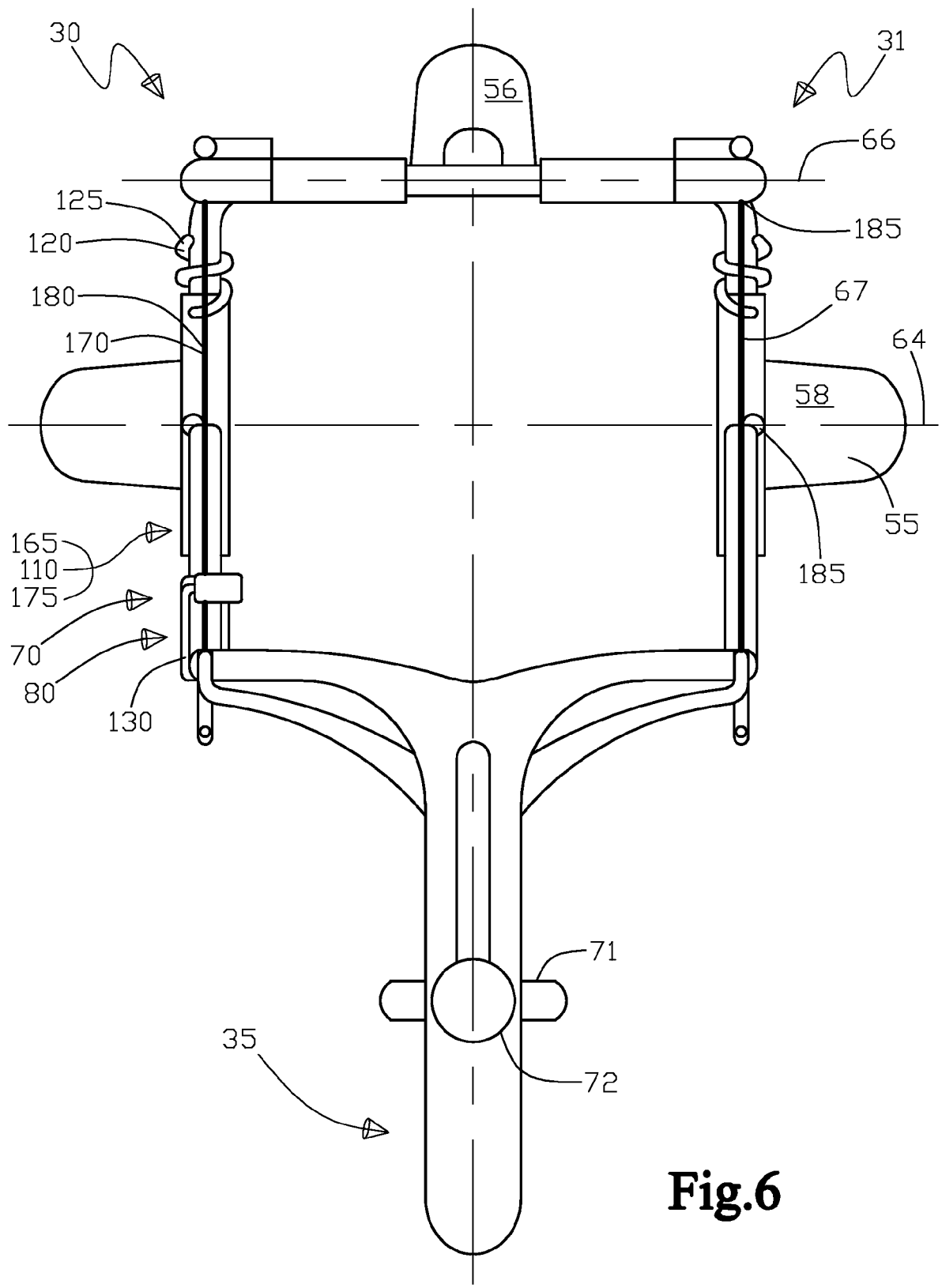
FIG. 6 shows a service provider end view of the examination apparatus including the flexible elements with the fingers in the open state and the structure in the compressed state.

With initial reference to FIG. 1 shown is a perspective view of the examination apparatus 30 or 31 including the flexible elements 170 with the fingers 55 in the stowed state 65 and the structure 35 in the free state 45. Continuing, FIG. 2 shows a perspective view of the examination apparatus 30 or 31 including the flexible elements 170 with the fingers 55 in the open state 70 and the structure 35 in the compressed state 50. Next, FIG. 3 shows a side elevation view of the examination apparatus 30 or 31 including the flexible elements 170 with the fingers 55 in the stowed state 65 and the structure in the free state 45. FIG. 4 shows a side elevation view of the examination apparatus 30 or 31 including the flexible elements 170 with the fingers 55 in the open state 70 and the structure 35 in the compressed state 50. Continuing further, FIG. 5 shows a service provider 250 end view of the examination apparatus 30 or 31 including the flexible elements 170 with the fingers 55 in the stowed state 65 and the structure 35 in the free state 45 and FIG. 6 shows a service provider 250 end view of the examination apparatus 30 or 31 including the flexible elements 170 with the fingers 55 in the open state 70 and the structure 35 in the compressed state 50.

Figure 7:
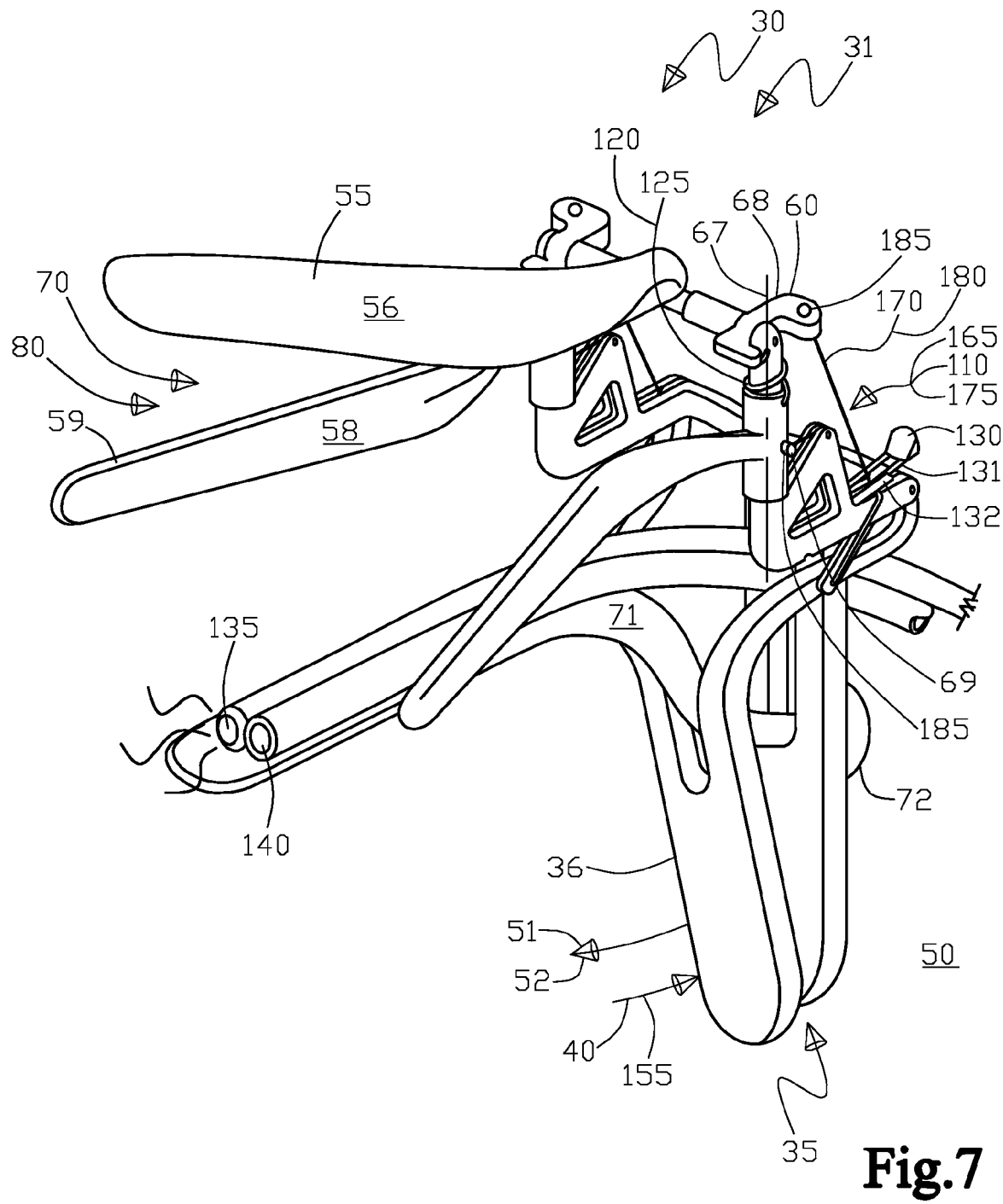
FIG. 7 shows a perspective view of the examination apparatus including the flexible elements with the fingers in the open state and the structure in the compressed state further comprising a means for fluid communication and a means for light communication both adjacent to a finger.
Figure 8:
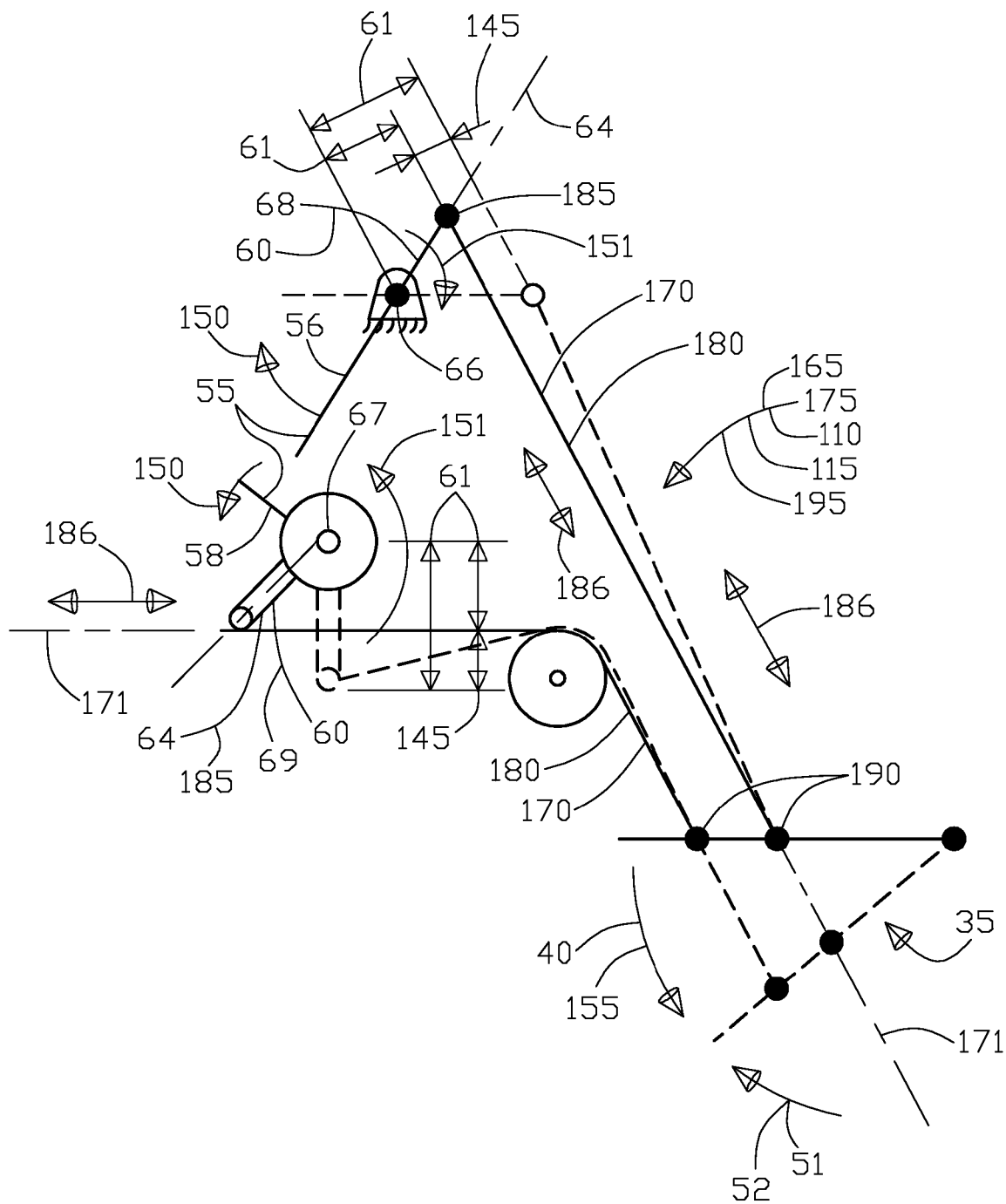
FIG. 8 is a kinematic schematic representation of the examination apparatus including the flexible elements, showing primarily a means for moving the fingers utilizing the structure, further the view for the second finger is rotated ninety degrees toward the viewer for pictorial clarity.
Figure 9:
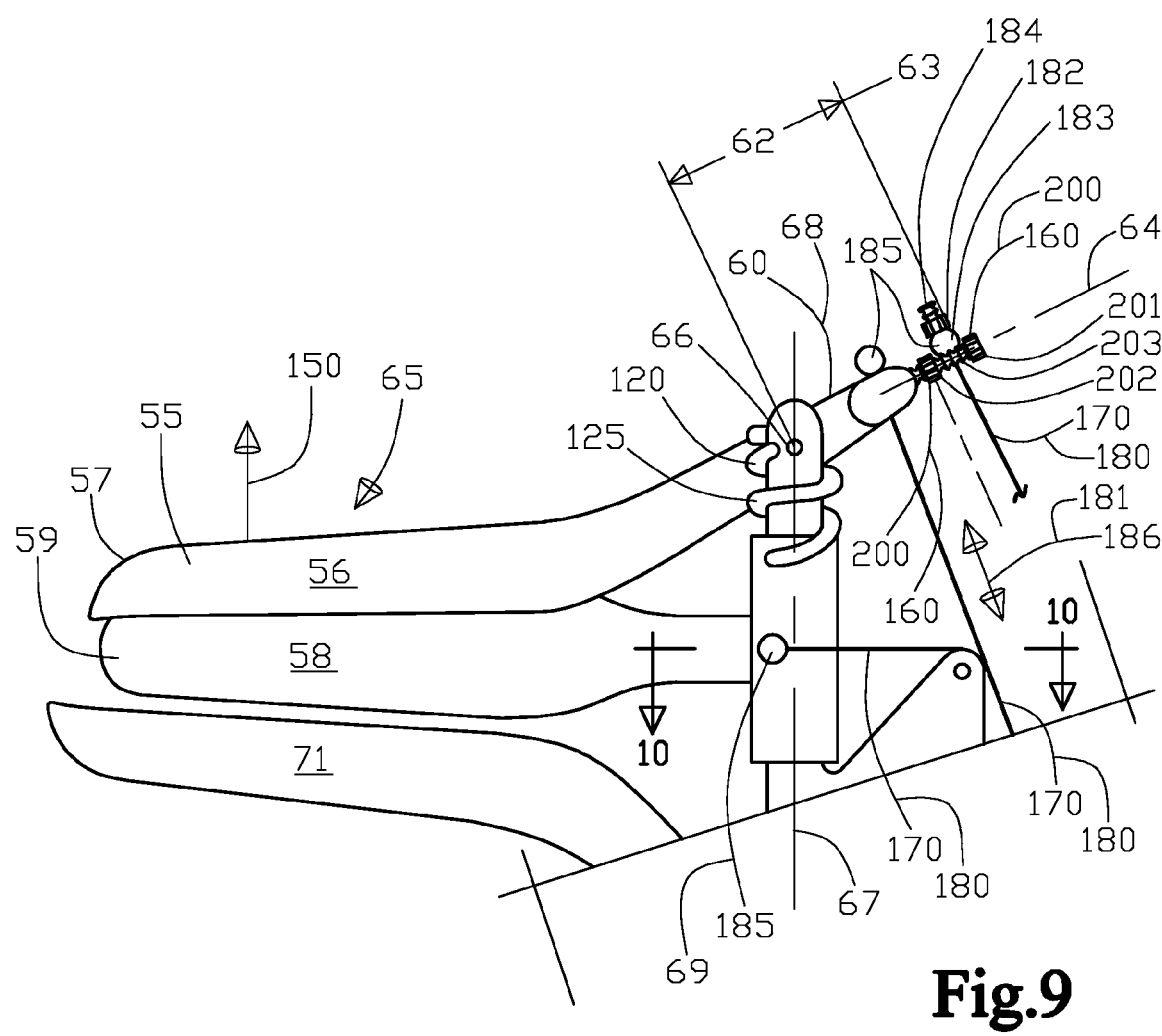
FIG. 9 shows a partial side elevation view of the examination apparatus including the flexible elements with the fingers in the stowed state and the structure in the free state, that further comprises a detail of the selectable increasing mechanical advantage as applied to a first finger.
Figure 10:
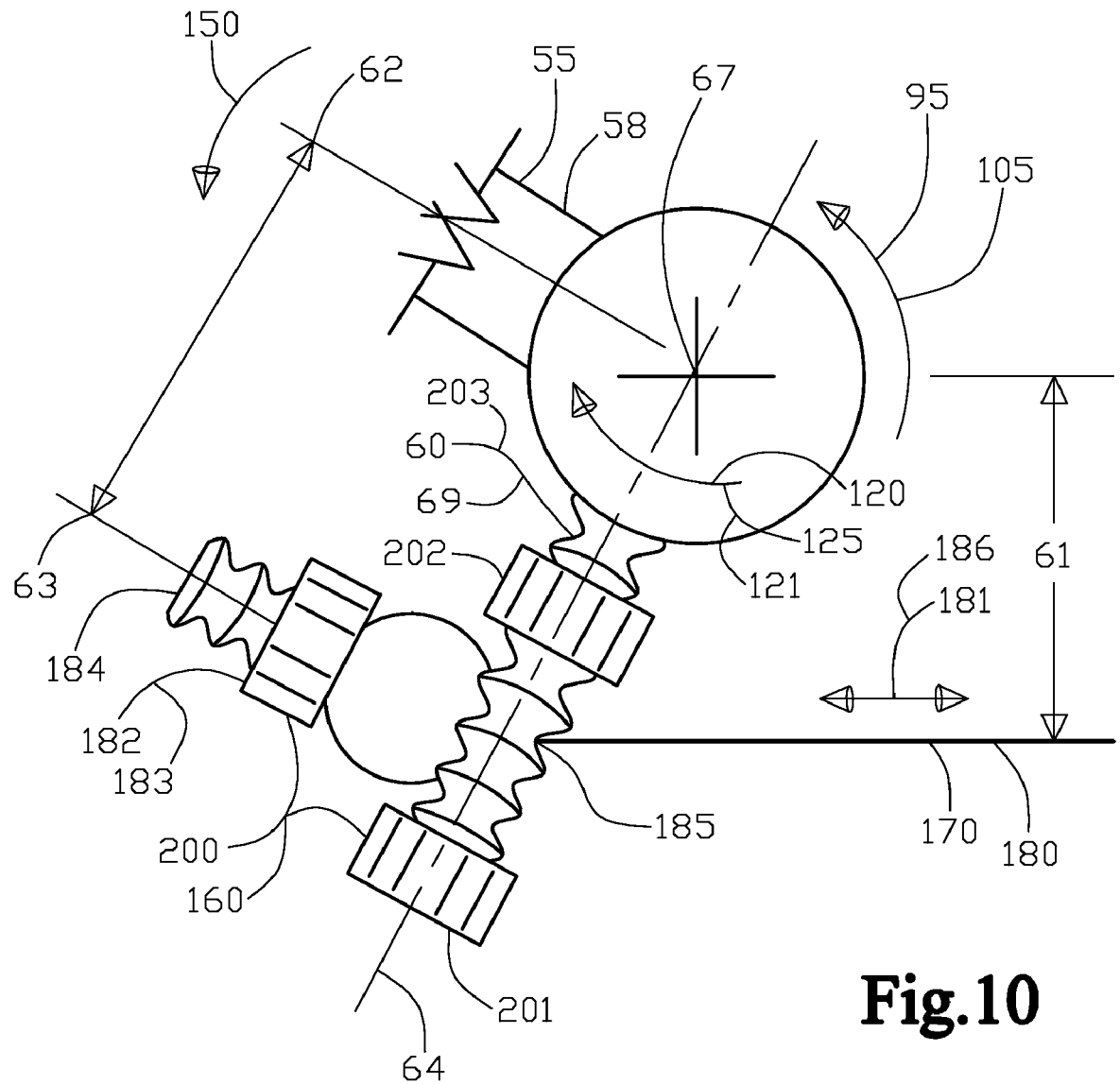
FIG. 10 is a section 10-10 view from FIG. 9 that further comprises a detail of the selectable increasing mechanical advantage as applied to a second finger.

Moving forward, FIG. 7 shows a perspective view of the examination apparatus 30 or 31 including the flexible elements 170 with the fingers 55 in the open state 70 and the structure 35 in the compressed state 50 further comprising a means 135 for fluid communication and a means 140 for light communication both adjacent to the finger 55. Following, FIG. 8 is a kinematic schematic representation of the examination apparatus 30 or 31 including the flexible elements 170, showing primarily a means 110 for moving the fingers 55 utilizing the structure 35, further the view for the second finger 58 is rotated ninety degrees toward the FIG. 8 viewer for pictorial clarity. Next, FIG. 9 shows a partial side elevation view of the examination apparatus 30 or 31 including the flexible elements 170 with the fingers 55 in the stowed state 65 and the structure 35 in the free state 45, that further comprises a detail of the selectable 160 increasing mechanical advantage as applied to a first finger 56 and FIG. 10 is a section 10-10 view from FIG. 9 that further comprises a detail of the selectable 160 increasing mechanical advantage as applied to a second finger 58.

Figure 11:
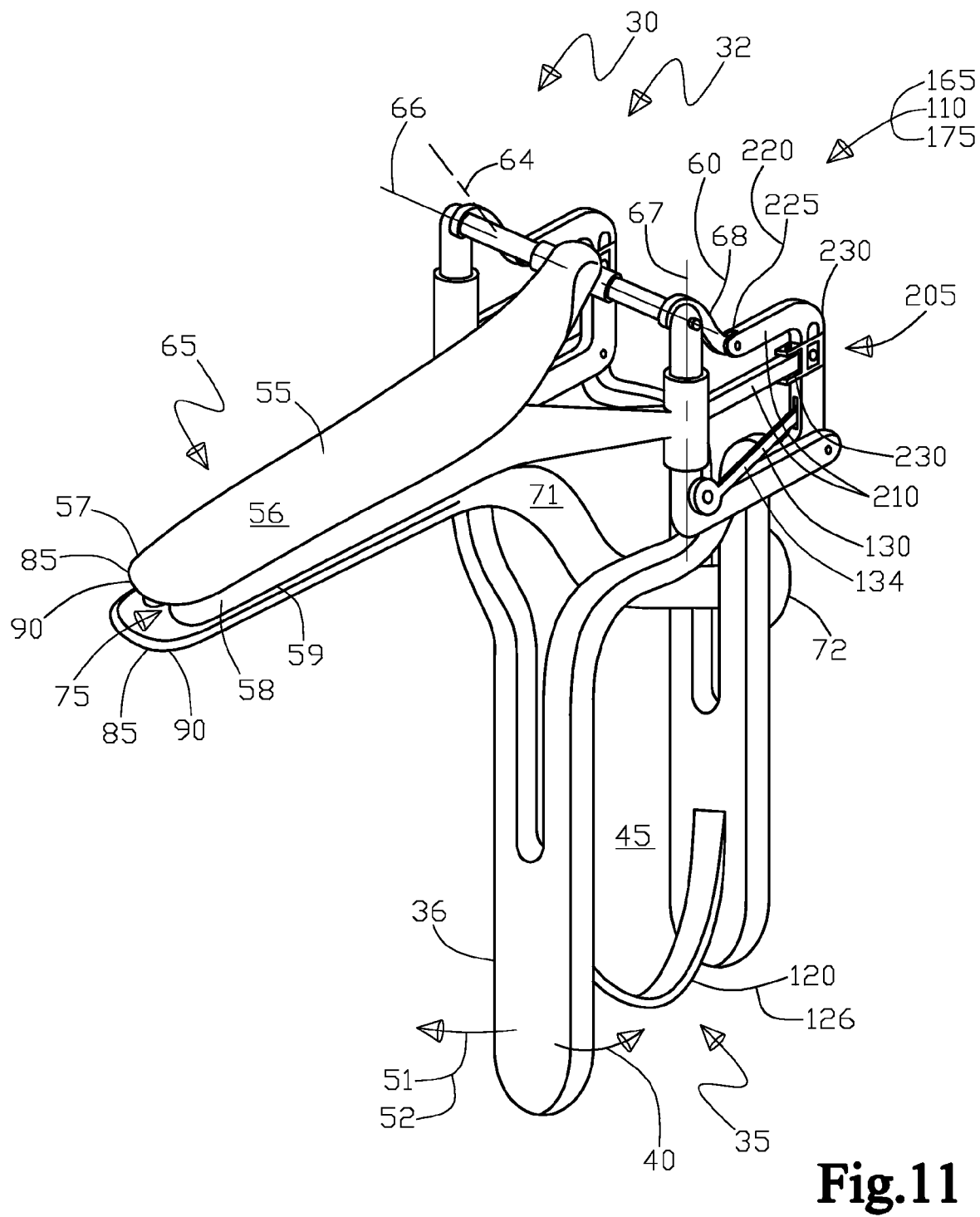
FIG. 11 shows a perspective view of the examination apparatus including the linkages with the fingers in the stowed state and the structure in the free state.
Figure 12:
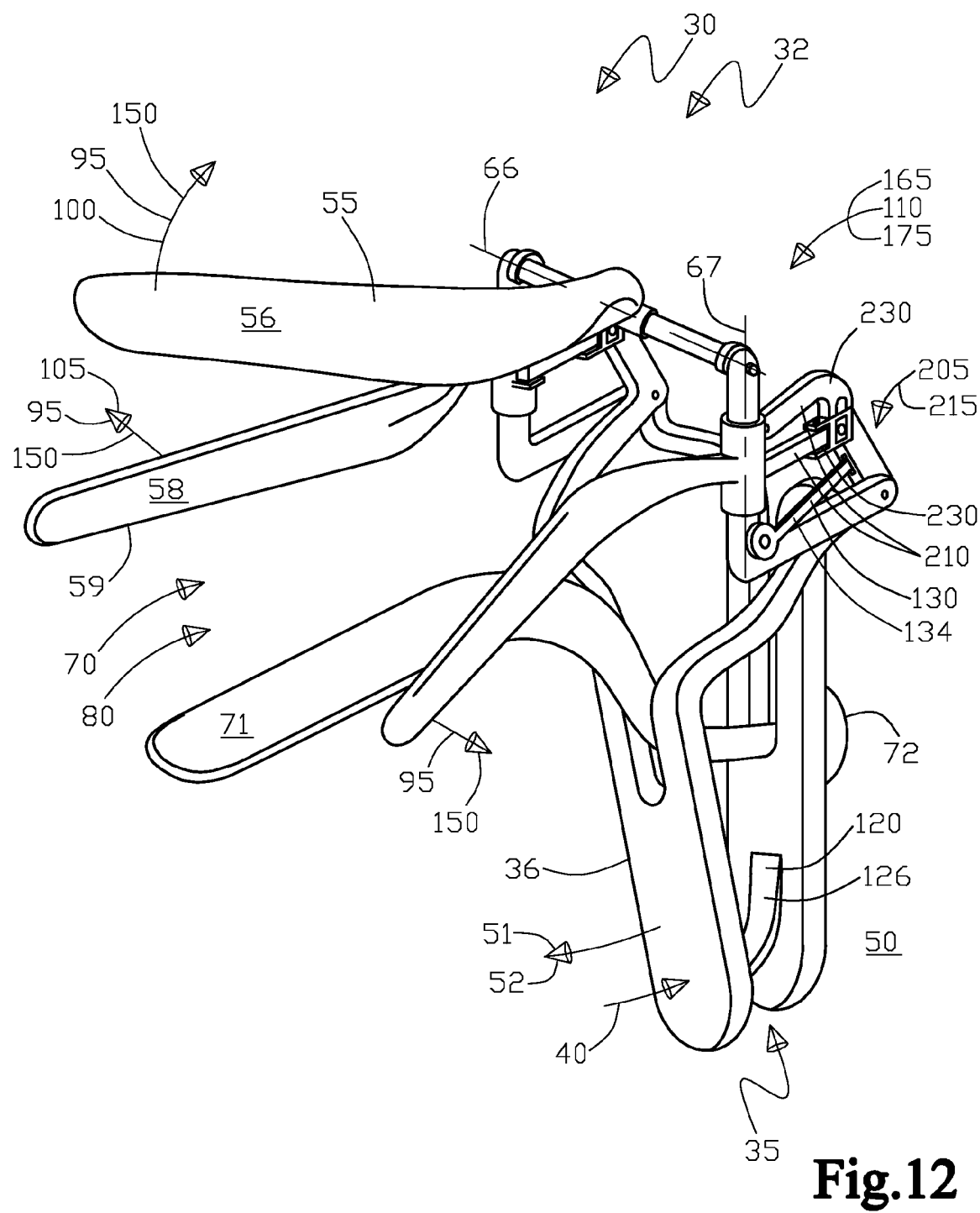
FIG. 12 shows a perspective view of the examination apparatus including the linkages with the fingers in the open state and the structure in the compressed state.
Figure 13:
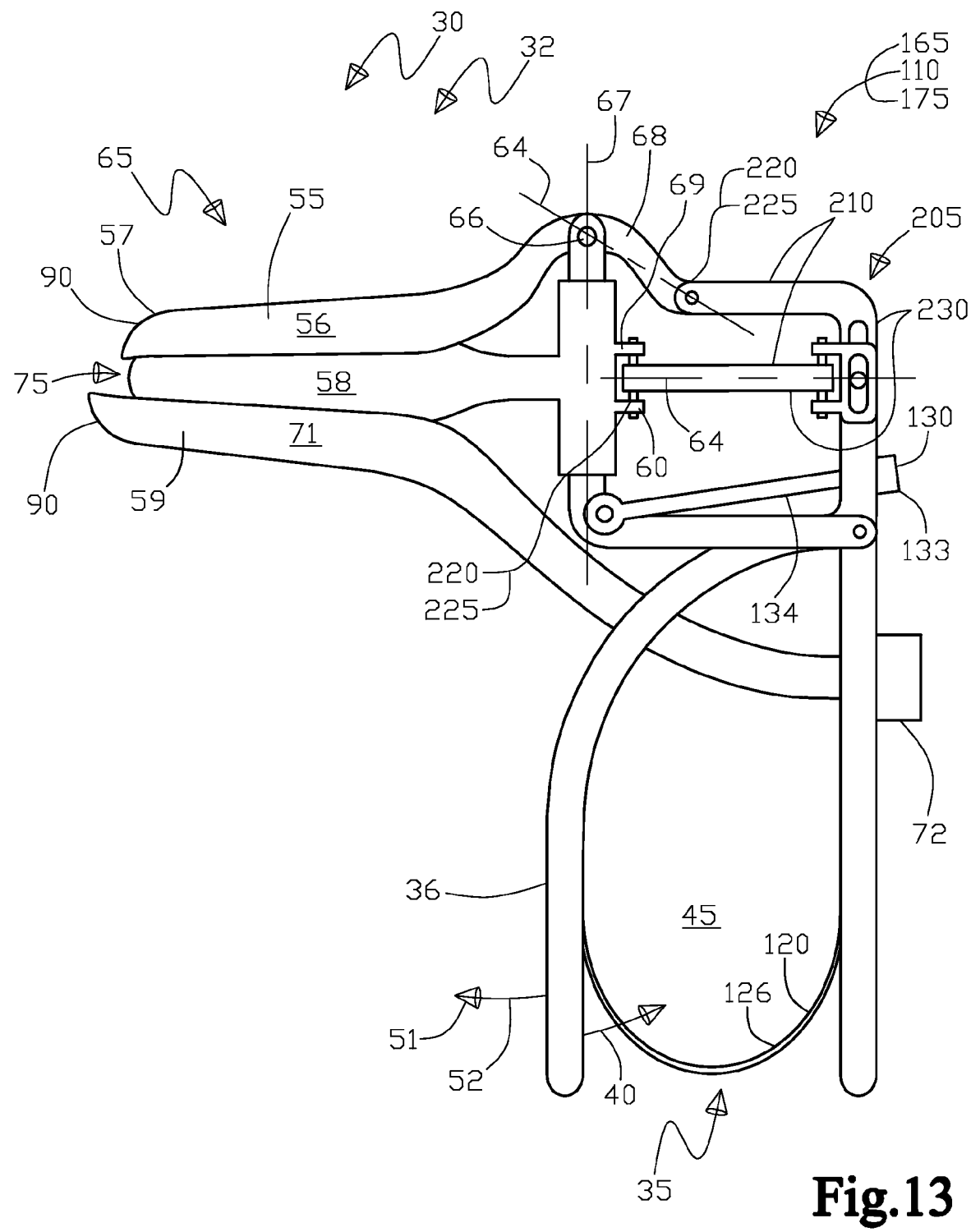
FIG. 13 shows a side elevation view of the examination apparatus including the linkages with the fingers in the stowed state and the structure in the free state.
Figure 14:
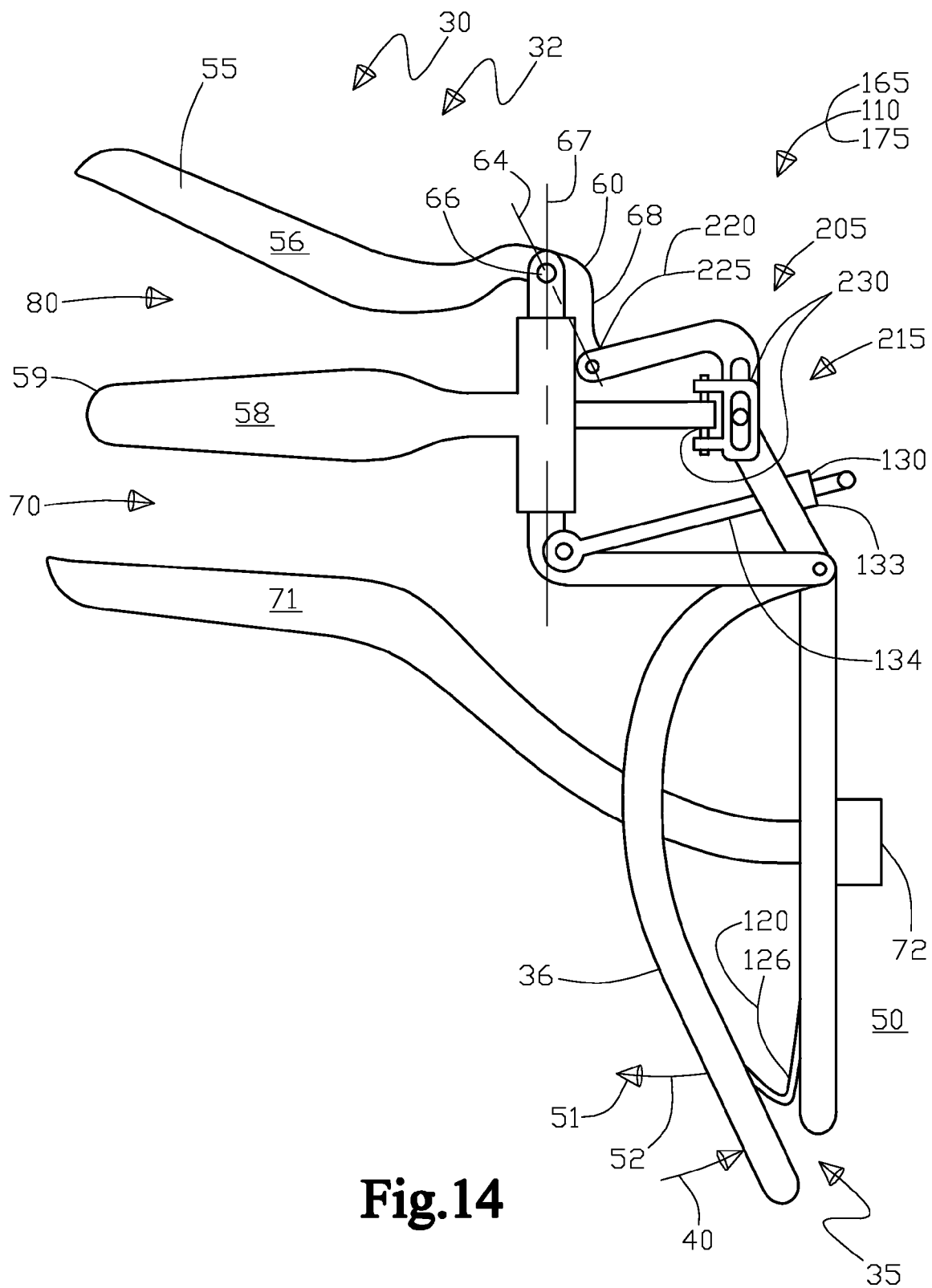
FIG. 14 shows a side elevation view of the examination apparatus including the linkages with the fingers in the open state and the structure in the compressed state.
Figure 15:
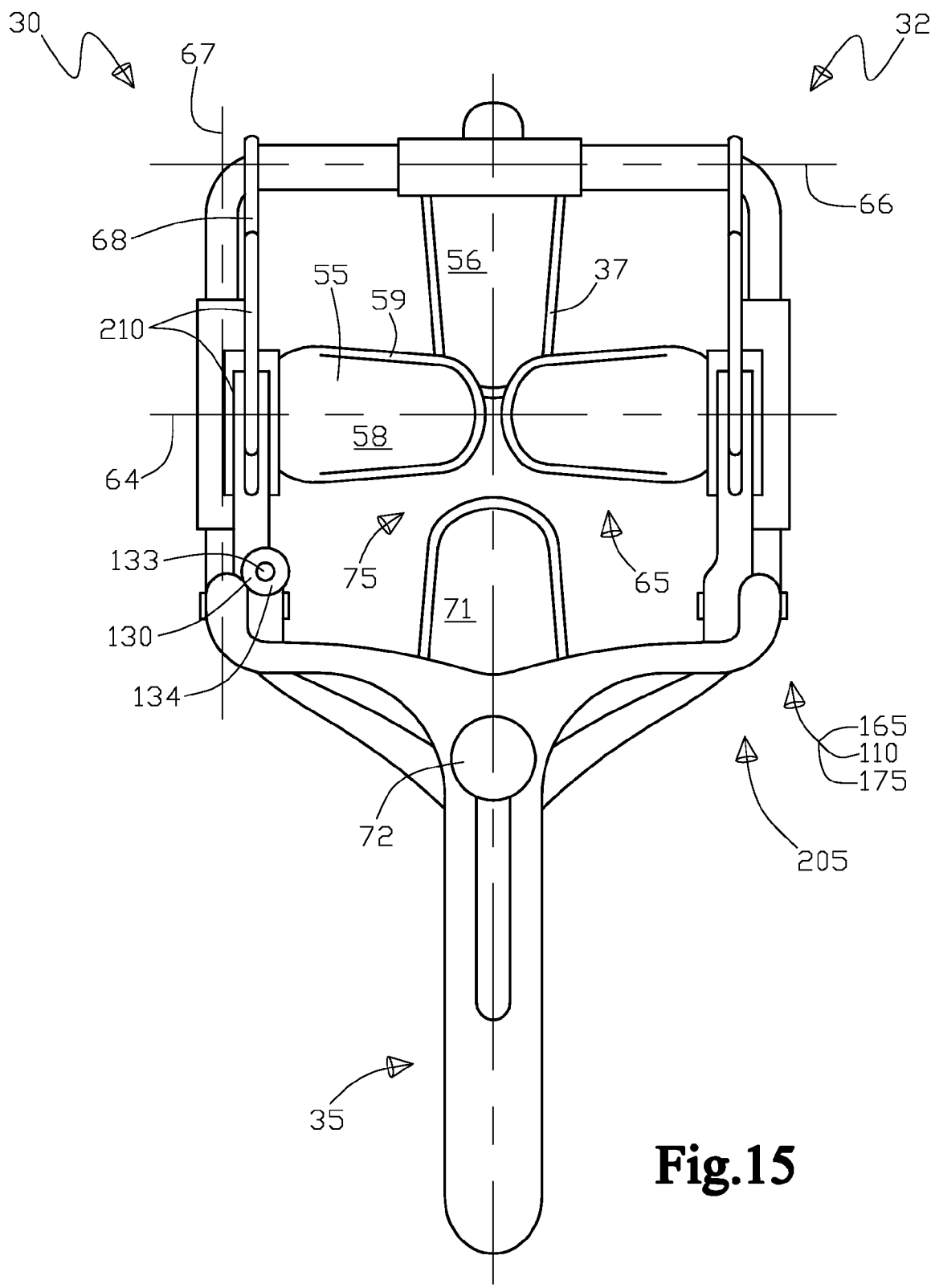
FIG. 15 shows a service provider end view of the examination apparatus including the linkages with the fingers in the stowed state and the structure in the free state.
Figure 16:
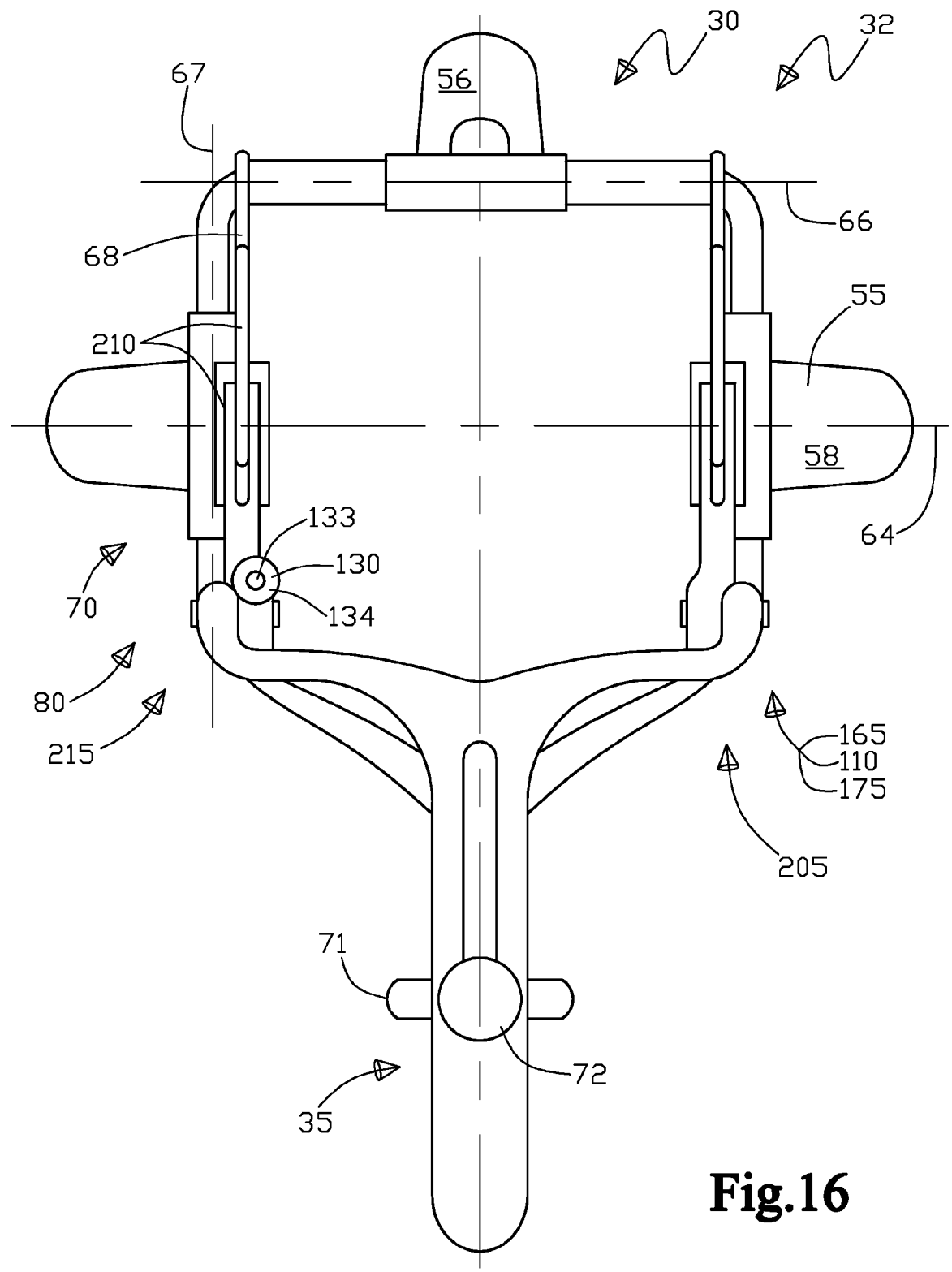
FIG. 16 shows a service provider end view of the examination apparatus including the linkages with the fingers in the open state and the structure in the compressed state.

Continuing, FIG. 11 shows a perspective view of the examination apparatus 30 or 32 including the linkages 210 with the fingers 55 in the stowed state 65 and the structure 35 in the free state 45 and FIG. 12 shows a perspective view of the examination apparatus 30 or 32 including the linkages 210 with the fingers 55 in the open state 70 and the structure 35 in the compressed state 50. Furthermore, FIG. 13 shows a side elevation view of the examination apparatus 30 or 32 including the linkages 210 with the fingers 55 in the stowed state 65 and the structure 35 in the free state 45 and FIG. 14 shows a side elevation view of the examination apparatus 30 or 32 including the linkages 210 with the fingers 55 in the open state 70 and the structure 35 in the compressed state 50. Yet further, FIG. 15 shows a service provider 250 end view of the examination apparatus 30 or 32 including the linkages 210 with the fingers 55 in the stowed state 65 and the structure 35 in the free state 45 and FIG. 16 shows a service provider 250 end view of the examination apparatus 30 or 32 including the linkages 210 with the fingers 55 in the open state 70 and the structure 35 in the compressed state 50.

Figure 17:
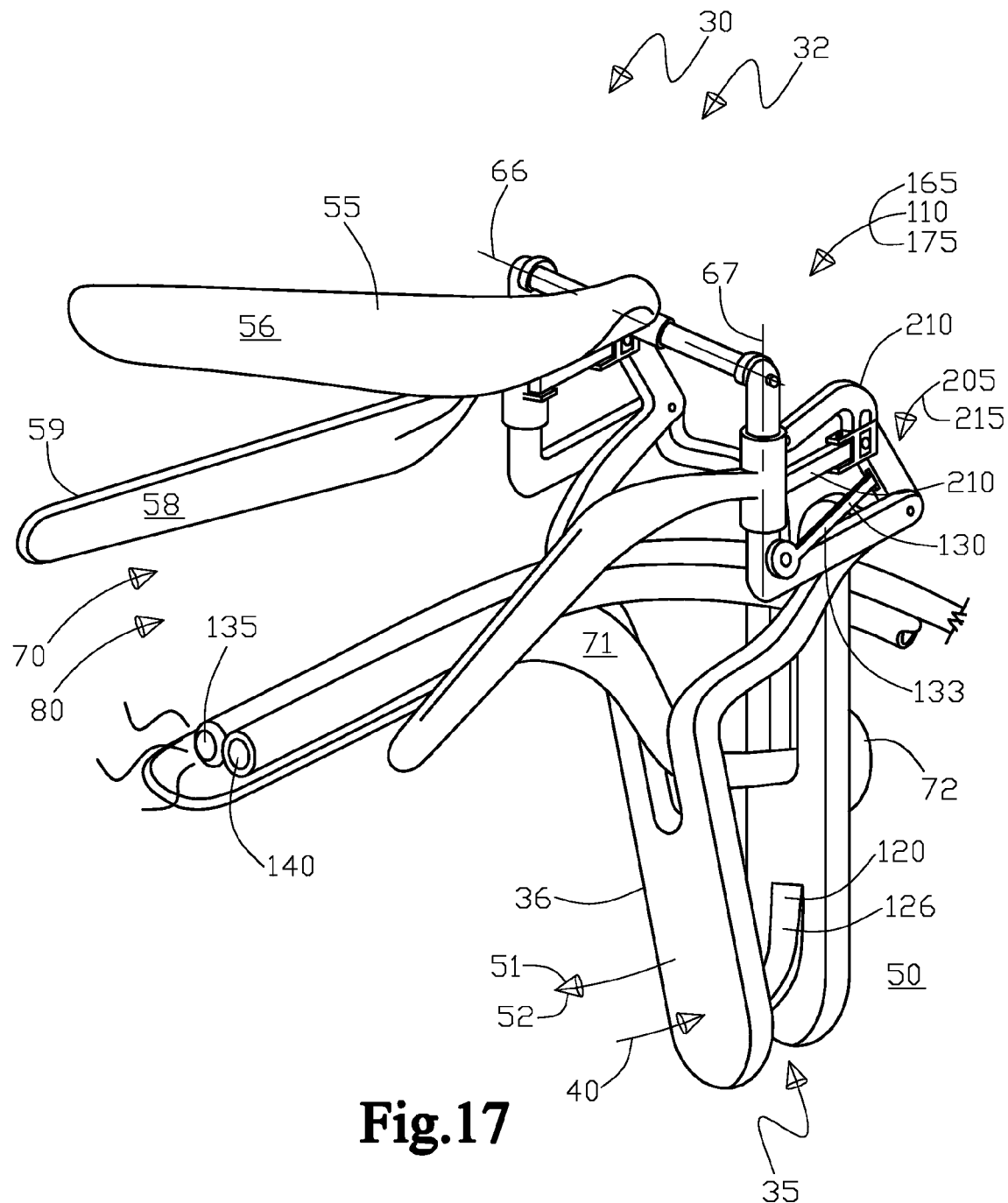
FIG. 17 shows a perspective view of the examination apparatus including the linkages with the fingers in the open state and the structure in the compressed state further comprising a means for fluid communication and a means for light communication both adjacent to a finger.
Figure 18:
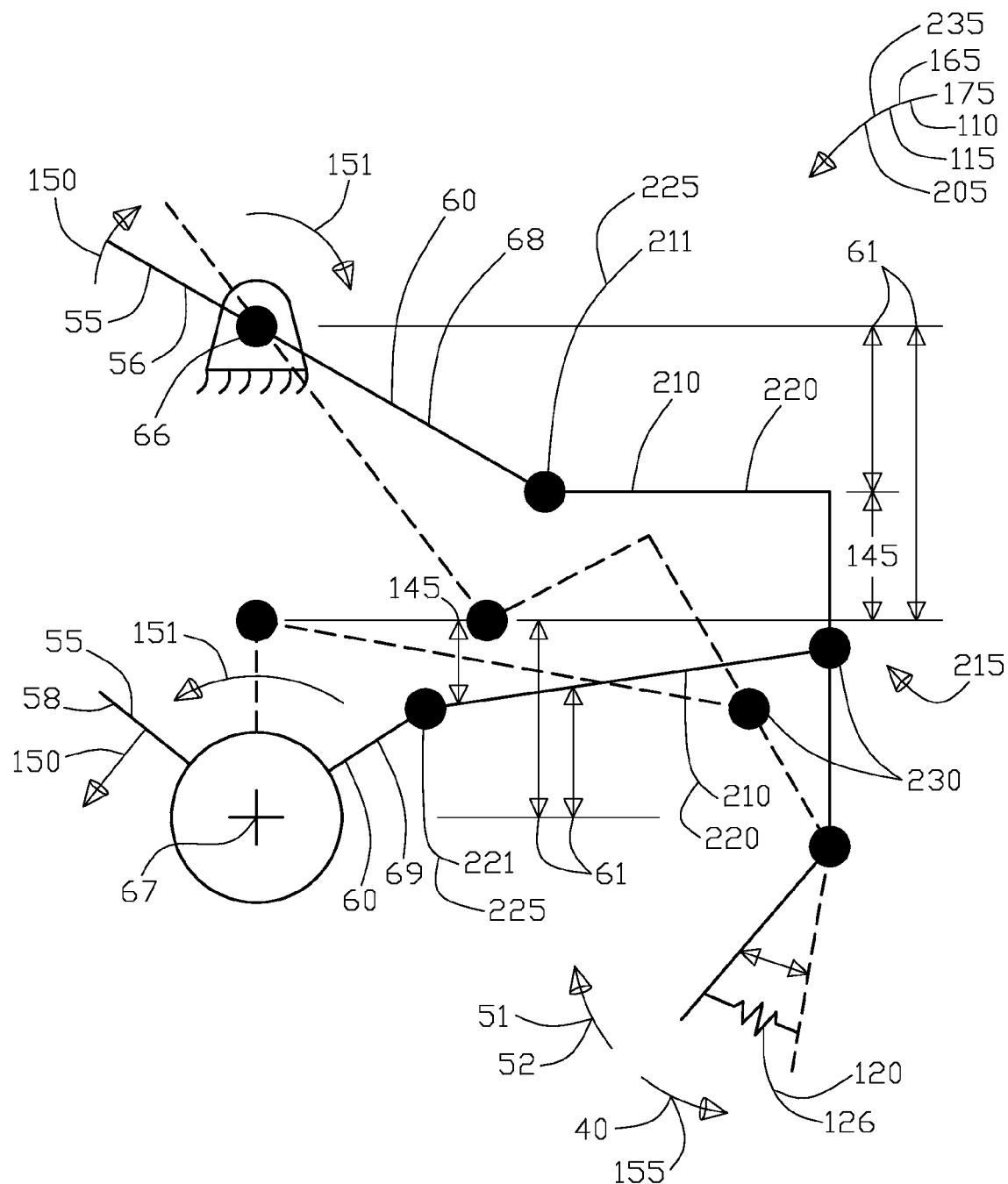
FIG. 18 is a kinematic schematic representation of the examination apparatus including the linkages, showing primarily a means for moving the fingers utilizing the structure, further the view for the second finger is rotated ninety degrees toward the viewer for pictorial clarity.
Figure 19:
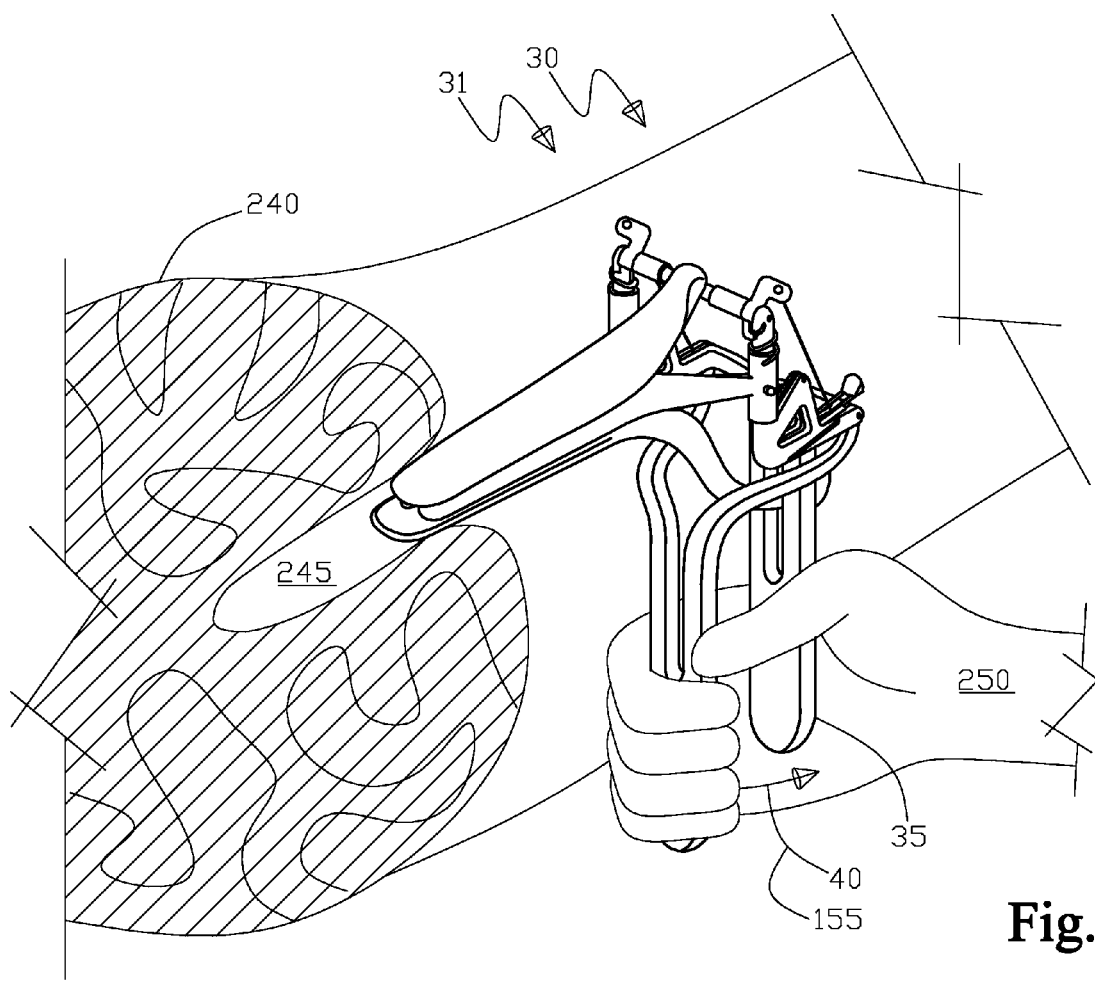
FIG. 19 shows a perspective use view of the examination apparatus including the flexible elements with the fingers in the stowed state and the structure in the free state, wherein a nested silhouette of the fingers in the stowed state is being inserted into an examination body cavity cross section of a creature or patient by a service provider.
Figure 20:
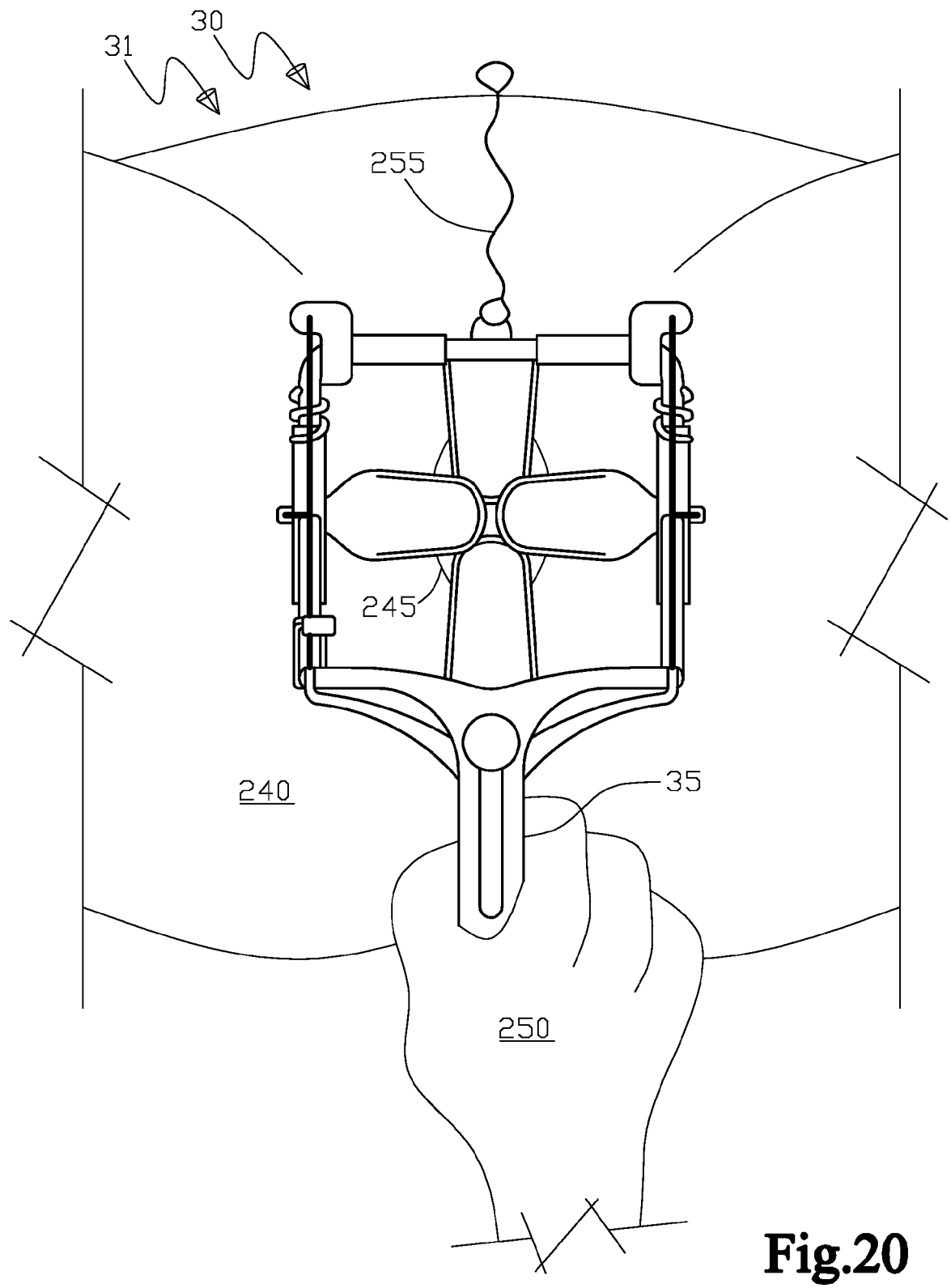
FIG. 20 shows the service providers view of the examination apparatus including the flexible elements with the fingers in the stowed state and the structure in the free state, wherein a nested silhouette of the fingers in the stowed state is being inserted into an examination body cavity of the creature or patient by a service provider.

Moving onward, FIG. 17 shows a perspective view of the examination apparatus 30 or 32 including the linkages 210 with the fingers 55 in the open state 70 and the structure 35 in the compressed state 50 further comprising a means 135 for fluid communication and a means 140 for light communication both adjacent to a finger 55. Further, FIG. 18 is a kinematic schematic representation of the examination apparatus 30 or 32 including the linkages 210, showing primarily a means 110 for moving the fingers 55 utilizing the structure 35, further the view for the second finger 58 is rotated ninety degrees toward the FIG. 18 viewer for pictorial clarity. Next, FIG. 19 shows a perspective use view of the examination apparatus 30 or 31 including the flexible elements 170 with the fingers 55 in the stowed state 65 and the structure 35 in the free state 45, wherein a nested profile 85 silhouette 90 of the fingers 55 in the stowed state 65 is being inserted into an examination body 240 cavity 245 shown in cross section of a creature or patient 240 by a service provider 250. Continuing, FIG. 20 shows the service providers 250 view of the examination apparatus 30 or 31 including the flexible elements 170 with the fingers 55 in the stowed state 65 and the structure 35 in the free state 45, wherein a nested profile 85 silhouette 90 of the fingers 55 in the stowed state 65 is being inserted into an examination body 240 cavity 245 of the creature or patient 240 by a service provider 250.

Figure 21:
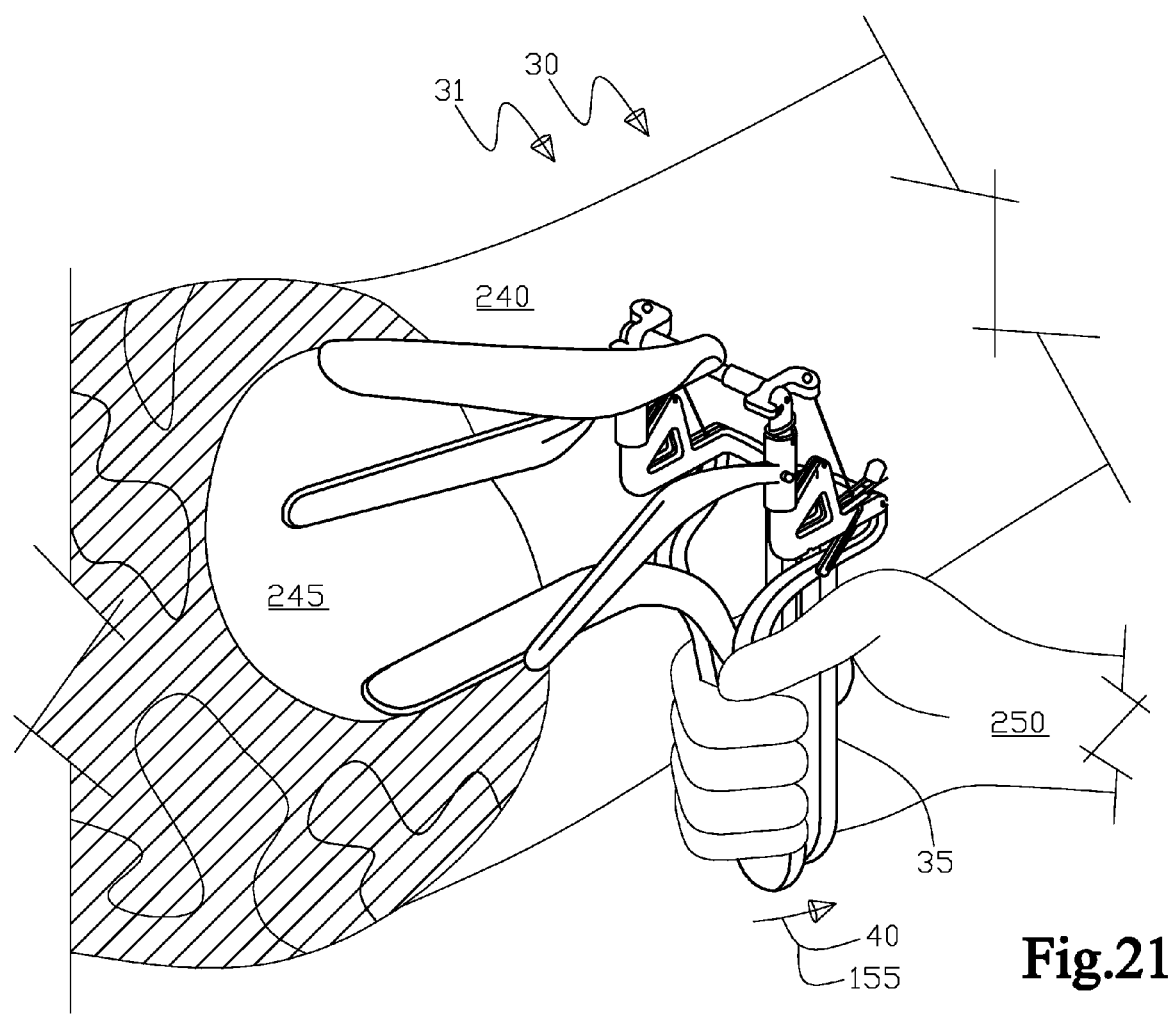
FIG. 21 shows a perspective use view of the examination apparatus including the flexible elements with the fingers in the open state and the structure in the compressed state, wherein the fingers in the open state have expanded the examination body cavity in cross section of the creature or patient by the service provider.
Figure 22:
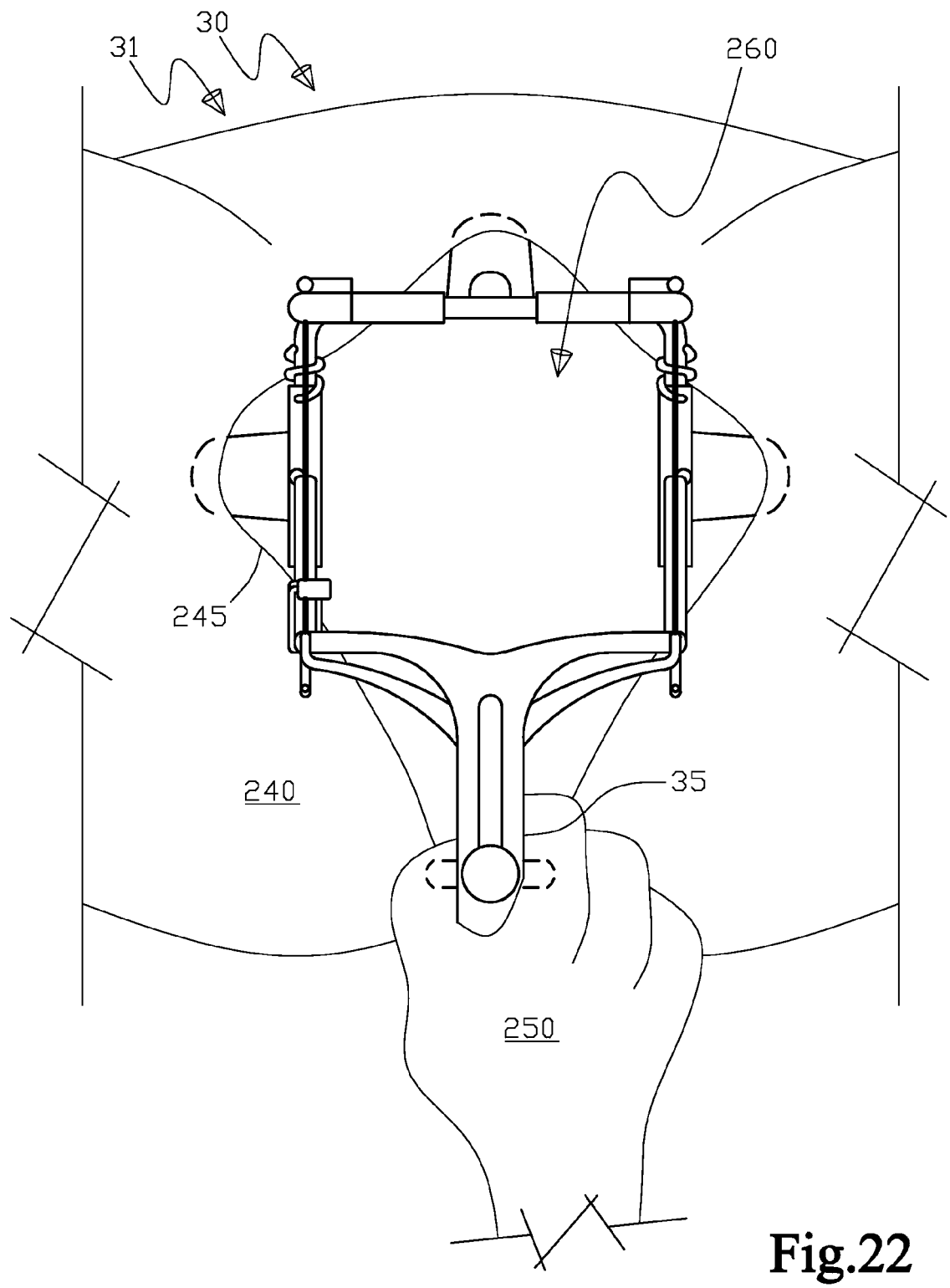
FIG. 22 shows the service providers field of view of the examination apparatus including the flexible elements with the fingers in the open state and the structure in the compressed state, wherein the fingers in the open state have expanded the examination body cavity of a creature or patient by the service provider.
Figure 23:
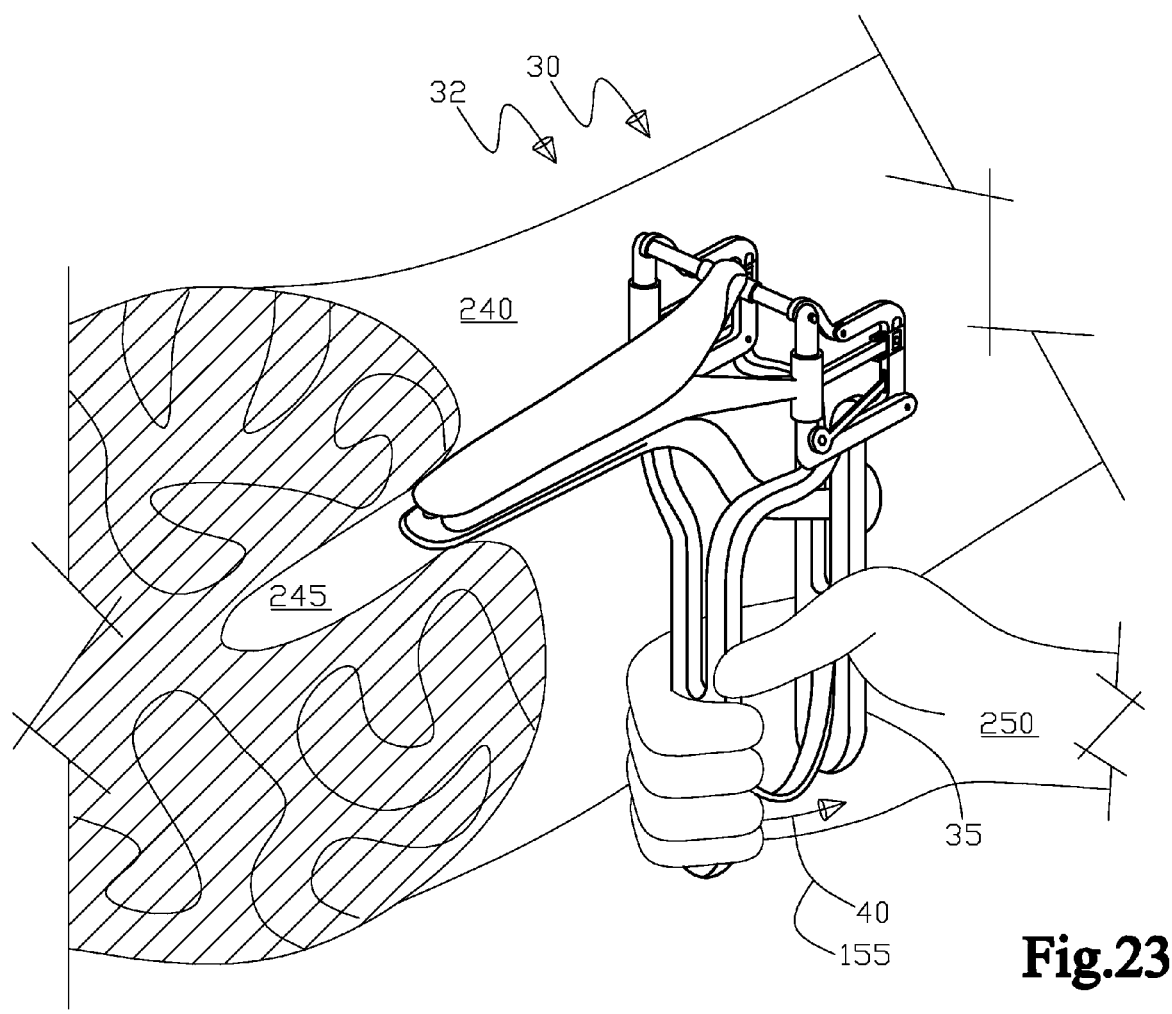
FIG. 23 shows a perspective use view of the examination apparatus including the linkages with the fingers in the stowed state and the structure in the free state, wherein the nested silhouette of the fingers in the stowed state is being inserted into the examination body cavity in cross section of the creature or patient by the service provider.

Furthermore, FIG. 21 shows a perspective use view of the examination apparatus 30 or 31 including the flexible elements 170 with the fingers 55 in the open state 70 and the structure 35 in the compressed state 50, wherein the fingers 55 in the open state 70 have expanded the examination body 240 cavity 245 shown in cross section of the creature or patient 240 by the service provider 250. Further, FIG. 22 shows the service providers 250 field of view of the examination apparatus 30 or 31 including the flexible elements 170 with the fingers 55 in the open state 70 and the structure 35 in the compressed state 50, wherein the fingers 55 in the open state 70 have expanded the examination body 240 cavity 245 of a creature or patient 240 by the service provider 250. Moving ahead, FIG. 23 shows a perspective use view of the examination apparatus 30 or 32 including the linkages 210 with the fingers 55 in the stowed state 65 and the structure 35 in the free state 45, wherein the nested profile 85 silhouette 90 of the fingers 55 in the stowed state 65 is being inserted into the examination body 240 cavity 245 shown in cross section of the creature or patient 240 by the service provider 250.

Figure 24:
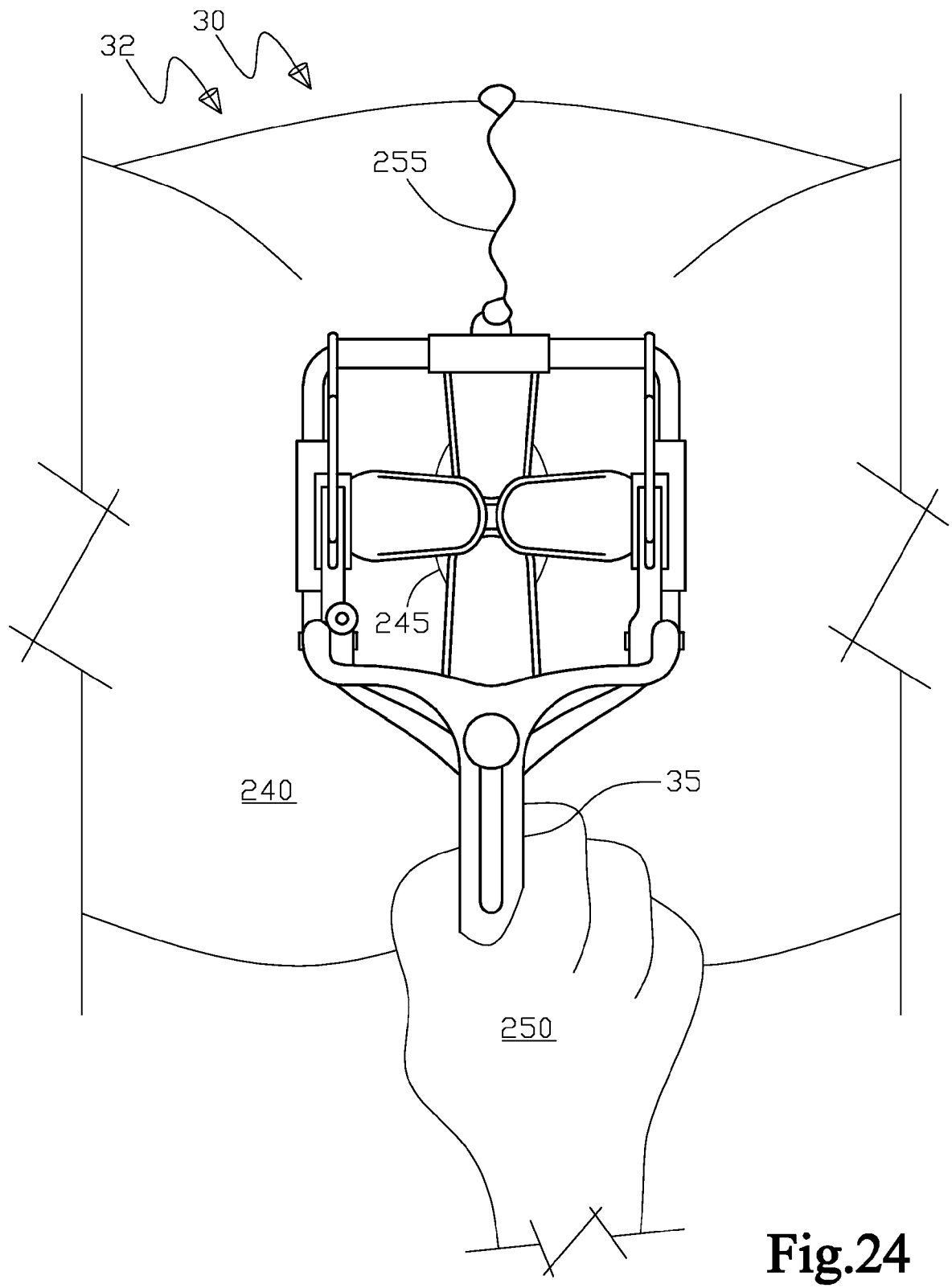
FIG. 24 shows the service providers view of the examination apparatus including the linkages with the fingers in the stowed state and the structure in the free state, wherein the nested silhouette of the fingers in the stowed state is being inserted into the examination body cavity of the creature or patient by the service provider.
Figure 25:
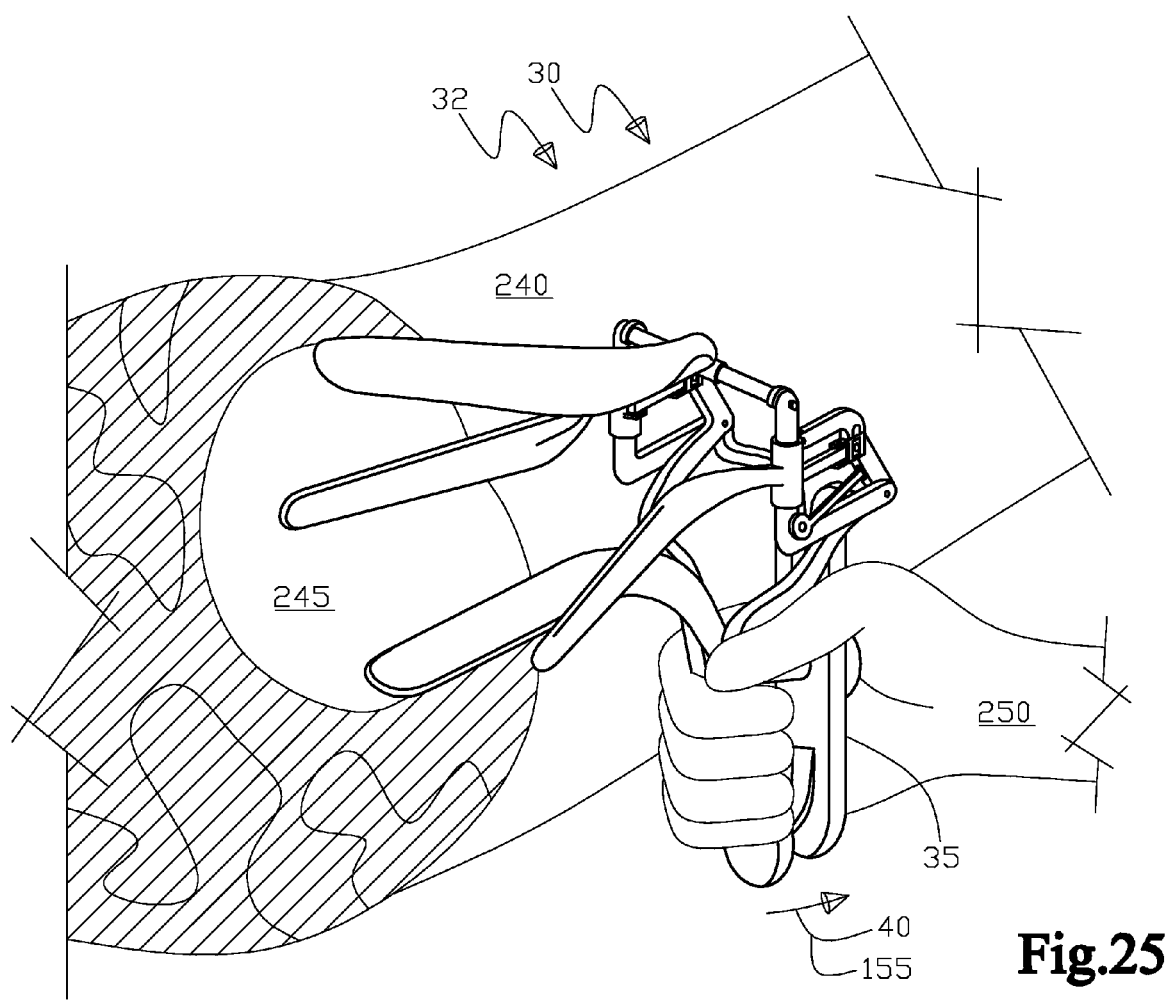
FIG. 25 shows a perspective use view of the examination apparatus including the linkages with the fingers in the open state and the structure in the compressed state, wherein the fingers in the open state have expanded the examination body cavity in cross section of the creature or patient by the service provider.
Figure 26:
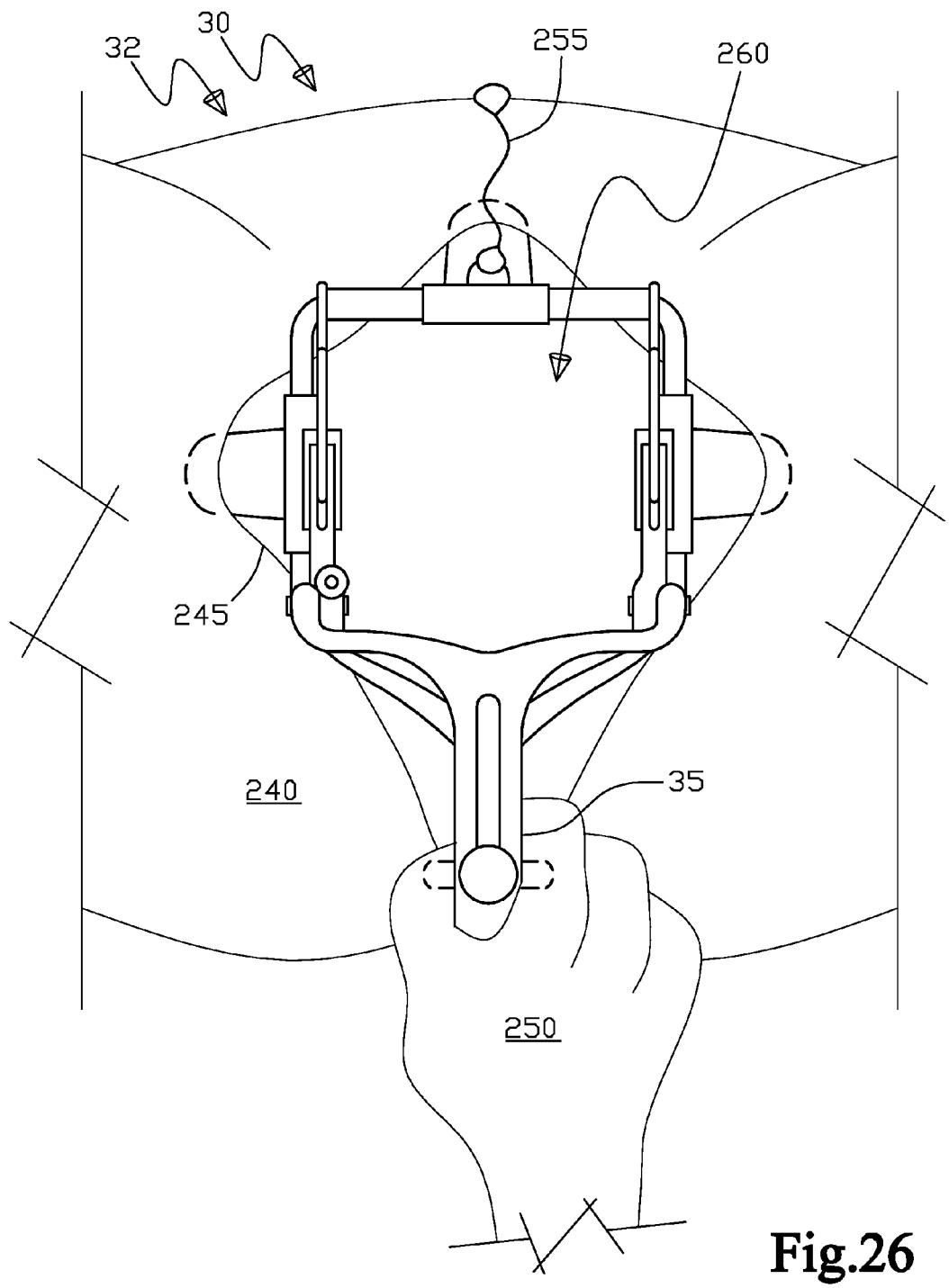
FIG. 26 shows the service providers field of view of the examination apparatus including the linkages with the fingers in the open state and the structure in the compressed state, wherein the fingers in the open state have expanded the examination body cavity of the creature or patient by the service provider.

Continuing, FIG. 24 shows the service providers 250 view of the examination apparatus 30 or 32 including the linkages 210 with the fingers 55 in the stowed state 65 and the structure 35 in the free state 45, wherein the nested profile 85 silhouette 90 of the fingers 55 in the stowed 65 state is being inserted into the examination body 240 cavity 245 of the creature or patient 240 by the service provider 250. Further, FIG. 25 shows a perspective use view of the examination apparatus 30 or 32 including the linkages 210 with the fingers 55 in the open state 70 and the structure 35 in the compressed state 50, wherein the fingers 55 in the open state 70 have expanded the examination body 240 cavity 245 shown in cross section of the creature or patient 240 by the service provider 250. Continuing onward, FIG. 26 shows the service providers 250 field of view of the examination apparatus 30 or 32 including the linkages 210 with the fingers 55 in the open state 70 and the structure 35 in the compressed state 50, wherein the fingers 55 in the open state 70 have expanded the examination body 240 cavity 245 of the creature or patient 240 by the service provider 250.

Broadly the present invention as best shown in FIGS. 1 through 18 of the examination apparatus 30, 31, and 32 includes a manually movable structure 35 having a first selective movement 40 from a free state 45 to a compressed state 50 and a second selective movement 51, being a return movement 52 from the compressed state 50 to the free state 45. Further included in the examination apparatus 30 are the plurality of fingers 55 disposed adjacent to the structure 35, the fingers 55 having a stowed state 65 and an open state 70, the stowed state 65 having a nested relationship 75 between the fingers 55 to reduce a silhouette 90 of a leading edge profile 85 of the plurality of fingers 55 in the stowed state 65, as best shown in FIGS. 1, 3, 5, 11, 13, and 15 for the nested relationship 75. Wherein the nested relationship 75 further facilitates easier insertion of the plurality of fingers 55 into the cavity 245 as best shown in FIGS. 19, 20, 23, and 24, by not requiring a precise fit between the fingers 55, this as opposed to fingers that are symmetrically disposed as to one another that do require a more precise fit to one another for a smooth and streamlined multiple finger body cavity insertion profile. The open state 70 requiring a selected sequential movement 95 of each finger 55 to one another to proceed from the nested relationship 75 to the open state 70.

Also included in the examination apparatus 30, 31, and 32 is the means 110 for moving the fingers 55 utilizing the structure 35, wherein the fingers 55 are moved from the stowed state 65 to the open state 70, as best shown in FIG. 1 to FIG. 2 and in FIG. 11 to FIG. 12. Wherein the means 110 for moving accommodates the selected sequential movement 95 in proceeding from the stowed state 65 to the open state 70 and reversing the sequential movement 95 in proceeding from the open state 70 to the stowed state 65. Further, in the means 110 for moving the fingers 55 is preferably sized and configured to facilitate the selected sequential movement 95 to include an initial movement 100 by a first finger 56 that allows the plurality of the fingers 55 to go from the stowed state 65 or nested relationship 75 to an un-nested 80 relationship of the plurality of fingers 55 followed by a further sequential movement 105 by a second finger 58 in proceeding to the open state 70, as best shown in as best shown in going from FIG. 1 to FIG. 2 and in going from FIG. 11 to FIG. 12.

Furthermore on the means 110 for moving the fingers 55 can also optionally further include a means 120 for urging the second finger 58 into the stowed state 65 through movement 121 as best shown in FIG. 10, thus operationally the means 120 can help ensure that the second finger 58 is nested 75 within the first finger 56 during the reverse movement of the fingers 55 in going from the open state 70 to the stowed state 65, as shown in going from FIG. 2 to FIG. 1 and in going from FIG. 12 to FIG. 11, thus the second finger 58 moves 121 to the nested relationship 75 prior to the first finger 56 moving to the nested relationship 75. Further, on the means 120 for urging the second finger 58 into the stowed state 65 is preferably a spring 125 or 126 as best shown in FIGS. 1 through 18. Alternatively, the means 120 could be elastomeric, a torsional spring, spiral spring, or any other equivalents for accomplishing the aforementioned urging function.

Returning to the nesting relationship 75, of the examination apparatus 30, 31, and 32, the nesting relation 75 preferably has the second finger 58 being sized and configured 59 to be disposed within a profile of first finger 56, as best shown in FIGS. 1, 3, 5, 11, 13, and 15, that results in the nested relationship 75 to form a silhouette 90 having a streamlined leading edge profile 85 for ease of insertion of the stowed 65 plurality of finger 55 into the body cavity 245, as best shown in FIGS. 19 and 20 and further in FIGS. 23 and 24.

Further, as best shown in FIGS. 1 to 7 and FIGS. 11 to 17 an adjustable finger 71 can be disposed upon the structure 35 via means 72 for adjusting the finger 71. The means 72 is preferably a thumb type screw that can allow finger 71 to move closer or further from the fingers 55 in the stowed state 65 as best shown in FIGS. 1, 3, 11, and 13. The means 72 can alternatively be any other type of adjustment such as rack and pinion, snap, frictional, and the like as long as the previously mentioned adjustability is maintained and the means 72 could withstand at least force 150 as against the involuntary movement of finger 71 along its adjustment path being closer or further from the fingers 55 in the stowed state 65 as best shown in FIGS. 1, 3, 11, and 13.

As an operational option the examination apparatus 30 can further comprise a lockable element 130 that is operational to selectively hold the plurality of fingers 55 at a selected position between the stowed state 65 and said open state 70, wherein the lockable element 130 is disposed adjacent to the means 110 such that plurality of fingers 55 are locked into a selected position that would be a fingers 55 position between as best shown in going from between FIG. 1 to FIG. 2 and in going from between FIG. 11 to FIG. 12. The lockable element 130 is preferably a flexible wire rod 131 that removably engages a toothed rack 132 such that the wire rod 131 urges itself to be removably engaged with the toothed rack 132 to be in a locked state, wherein the flexible wire 131 can be manually disengaged from the toothed rack 132 by the service provider 250 to unlock the lockable element 130 and allow the plurality fingers 55 to move freely between the stowed state 65 and the open state 70, as best shown in FIGS. 1, 2, 3, 4, and 7. Alternatively, the lockable element 130 can be a thumb nut 133 threadably engaged to a threaded rod 134 as best shown in FIGS. 11 through 17, wherein the thumb nut 133 is manually adjusted along the rod 134 to selectively hold the plurality of fingers 55 at a selected position between the stowed state 65 and said open state 70. Furthermore the lockable element 130 can be other arrangements as well that could include various clamping devices and the like.

On the materials of construction for the examination apparatus 30, 31, or 32 the structure 35 being preferably constructed of stainless steel, however, alternatively the structure 35 can be constructed of partially or completely of a non-electrically conductive material such as a composite or polymer. Further, on the structure 35 another alternative for the materials of construction could be a non-heat transfer material that could also be a composite or polymer. Other materials of construction could be used for the structure 35 as long as the functional requirements are meet of adequate strength for a manual compression through movements 40 and 51 by the service provider 250 and be autoclaveable for sterilization purposes. On the materials of construction for the examination apparatus 30, 31 or 32 the plurality of fingers 55 are preferably constructed of stainless steel, however, alternatively the fingers 55 can be constructed of partially or completely of a non electrically conductive material such as a composite or polymer. Further, for the plurality of fingers 55 another alternative for the materials of construction being constructed of partially or completely of a non-heat transfer material that could also be a composite or polymer. Other materials of construction being partially or completely constructed of, could be used for the plurality of fingers 55 as long as the functional requirements are meet of adequate strength for a expanding the body cavity 245 via manual force as exerted by the manual compression in movement 40 and 51 of the structure 35 by the service provider 250 and also be autoclavable for sterilization purposes.

Referring to FIGS. 7 and 17, shown is an option for adding the means 135 for fluid communication positioned adjacent to any one of the plurality of fingers 55 and the means 140 for light communication positioned adjacent to any one of the plurality of fingers 55. The means 135 for fluid communication is operational to remove or add fluids to the body cavity 245, as shown in use in FIGS. 21 and 25 as desired for various procedures. The means 135 for fluid communication is preferably a flexible tube that can be disposable and removably engagable to the fingers 55 or affixed and autocleaveable, the means 135 and can optionally be anything else that can meet the disclosed functional requirements. The means 140 for light communication is operational to add light to the body cavity 245, as shown in use in FIGS. 21 and 25 as desired for various examination procedures. The means 140 for light communication is preferably a fiber optic type tube that can be disposable and removably engagable to the fingers 55 or affixed and autoclavable, the means 140 can be optionally be anything else that can meet the disclosed functional requirements.

A further option for the means 110 for moving the fingers 55 is sized and configured to have an increasing mechanical advantage 145 in proceeding from the stowed state 65 to the open state 70, as best shown in FIGS. 8 and 18. Wherein the increasing mechanical advantage 145 is between the manually movable structure 35 and the plurality of fingers 55 that is operational to increase an opening force 150 of at least one of the plurality of fingers 55 from the stowed state 65 to the open state 70 for a substantially fixed manual force 155 on the structure 35 in proceeding from the stowed state 65 to the open state 70. Focusing again upon FIGS. 8 and 18, the increasing mechanical advantage 145 occurs due to a dynamic length change 61 of the moment arm 60 as viewed as the effective distance between the pivotal axis 66 and pivotal axis 67 and the flexible element 170 or linkages 210 cable adjacent portion 185 or pivotal connection 211 respectively, that applies to examination apparatus embodiments 30, 31, and 32. Looking in particular at FIG. 8 for the flexible elements 170 of the examination apparatus 31, the moment arm 60 at any given static position forms a constant moment arm length between the pivot 66 and the cable attachment point 185 when viewed perpendicular to the moment arm axis 64, however a dynamic moment arm length change 61 occurs when the moment arm 60 actively pivots about the pivotal axis 66 swinging the moment arm 60 through an arc type of motion 151 wherein the flexible element 170 moves 186 lengthwise in a juxtapose manner, i.e. parallel to its original position, and in this scenario the dynamic moment arm length 61 changes by an amount equal to the mechanical advantage distance 145 when viewed perpendicular to the flexible element 170 axis 171 as shown in length change 61 in FIG. 8.

The effect of this length change 61 is to change the finger 55 applied force 150 with a substantially constant amount of force 155 manually applied to the structure 35, as best shown in FIG. 8 in comparing the solid and dashed lines for two positions of the moment arm 60 and the flexible element 170. The benefit of the aforementioned length change 61 or dynamic moment arm is to have the finger 55 force 150 increase for instance as the finger 55 meets more opening force 150 resistance from the body cavity 245 the further the finger 55 progresses from the stowed state 65 to the open state 70, while at the same time only requiring a substantially constant force 155 manually placed upon the structure 35 by the service provider 250. Note that this dynamic moment arm length change 61 and aforementioned benefit applies equally well to the first finger 56 and the second finger 58 both as shown in FIG. 8, wherein basically the primary difference between the first finger 56 and the second finger 58 is their respective axis of pivotal rotation 66 and 67 being about ninety degrees apart, wherein the basic workings of the means 110 is substantially the same for the first finger 56 and the second finger 58.

Thus as best shown in FIG. 8, the means 110 is preferably comprised of the structure 35 that is manually put through the first selective movement 40 by the service provider 250, wherein this first selective movement 40 translates into flexible element 170 through motion 186 that pivotally attaches 185 to the moment arm 60 that acts through pivotal axis 66 and 67 ultimately resulting in finger 55 force 150 for both the first finger 56 and the second finger 58. Typically the flexible elements 170 are preferably cables 180 for strength, flexibility, light weight, and the ability to be autoclaved, the preferred cables 180 are any combinations or singular material that can meet the functional requirements disclosed especially pertaining to accommodating force 150 and autoclaving. Other ways to accomplish the means 110 would be acceptable also that could include shafting in conjunction with gear drives, or other cable/linkage arrangements that would accomplish the function of moving the fingers 55 from the stowed state 65 to the open state 70 and vice versa.

Looking at particular to FIGS. 9 and 10 in conjunction with FIG. 8, as a further option on the means 110 for moving the fingers 55 can be sized and configured to have a selectable increasing mechanical advantage 160 in proceeding from the stowed state 65 to said open state 70. Wherein the selectable increasing mechanical advantage 160 is between the manually movable structure 35 and the plurality of fingers 55 that is operational to selectably increase an opening force 150 on at least one of the plurality of fingers 55 from the stowed state 65 to the open state 70 for a substantially fixed manual force 155 on the structure 35 in proceeding from the stowed state 65 to 70 open state.

Starting with FIG. 9, the means 110 selectable increasing advantage 160 is preferably a selectable device 200 that utilizes a threaded portion 203 of the moment arm that is threadably engaged to both a lock nut 202 and a retaining nut 201, wherein the nuts 201 and 202 sandwich the flexible element 170, thereby facilitating a selectable change in moment arm length 62 that is operational to vary the finger 55 force 150 initially from the stowed state 65 of the fingers 55 with a given manual substantially constant force 155 from the service provider 250 on the structure 35 that resolves itself through the flexible element 170 movement 186 with the resulting increase or decrease in moment arm 60 length 62 facilitating a change in finger 55 force 150 throught the finger 55 movement from the stowed state 65 to the open state 70. Alternatives to the selectable device 200 could include a snap adjustment, a ratcheting arrangement, or any other device that could accomplish the selectable increasing advantage 160 that is autoclavable and can withstand the substantially constant force 155. Note that this is distinguished from the dynamic change in moment arm length 61 that is not due to the adjustment of the nuts 201 and 202, as the dynamic moment arm length 61 change is from the pivotal movement of the moment arm 60 through movement 151 not being due to the device 200. Also, concerning FIG. 10, the same disclosure would apply as used for FIG. 9, with the distinction being that FIG. 9 is for the first finger 56 and FIG. 10 is for the second finger 58.

Further, another optional adjustment for the means 110 could be utilized as is shown in FIGS. 9 and 10 also, in looking specifically at the cable nut 183 that is threadably engaged to a portion 184 of the cable to allow for adjustment of the cable 180 length 181 in relation to the finger 55 to accommodate variance in the finger 55 positions for the stowed state 65 and the open state 70 and also to allow adjustability in the sequential movement 95 and 105 specifically for the first finger 56 to un-nest 75 prior to the second finger 58 un-nesting 75 to better facilitate finger 55 movement from the stowed state 65 to the open state 70. Focusing on FIGS. 20 and 24, the retention element 255 is shown that is optional for retaining the examination apparatus 30, 31, or 32 to the creature or patient 240 or to an article disposed upon the creature or patient 240, wherein the retention element 255 has a removable engagement to the creature or patient 240.

Continuing in looking at the examination apparatus, in alternative embodiment 32, as shown in FIGS. 11 through 18 includes a manually movable structure 35 having a first selective movement 40 from a free state 45 to a compressed state 50 and a second selective movement 51, being a return movement 52 from the compressed state 50 to the free state 45. Further included in the examination apparatus 32 are the plurality of fingers 55 disposed adjacent to the structure 35, the fingers 55 having a stowed state 65 and an open state 70, the stowed state 65 having a nested relationship 75 between the fingers 55 to reduce a silhouette 90 of a leading edge profile 85 of the plurality of fingers 55 in the stowed state 65, as best shown in FIGS. 11, 13, and 15 for the nested relationship 75, wherein the nested relationship 75 further facilitates easier insertion of the plurality of fingers 55 into the cavity 245 as best shown in FIGS. 23, and 24, by not requiring a precise fit between the fingers 55, this as opposed to fingers that are symmetrically disposed as to one another that do require a more precise fit to one another for a smooth multiple finger body cavity insertion profile. The open state 70 requiring a selected sequential movement 95 of each finger 55 to one another to proceed from the nested relationship 75 to the open state 70.

Furthermore on the means 110 for moving the fingers 55 can also optionally further include a means 120 for urging the second finger 58 into the stowed state 65 through movement 121 as best shown in FIG. 18, thus operationally the means 120 can help ensure that the second finger 58 is nested 75 within the first finger 56 during the reverse movement of the fingers 55 in going from the open state 70 to the stowed state 65, as shown in going from FIG. 12 to FIG. 11 and in going from FIG. 14 to FIG. 13, also in going from FIG. 16 to FIG. 15, thus the second finger 58 moves 121 to the nested relationship 75 prior to the first finger 56 moving to the nested relationship 75. Further on the means 120 for urging the second finger 58 into the stowed state 65 is preferably a spring 126 as best shown in FIGS. 11 through 14 and FIG. 17. Alternatively, the means 120 could be elastomeric, a torsional spring, spiral spring, or any other equivalents for accomplishing the aforementioned urging function.

The examination apparatus embodiment 32 also includes an assemblage 205 for moving the plurality of fingers 55 from the stowed state 65 to the open state 70, wherein the assemblage 205 includes a plurality of linkages 210 that communicate movement 215 from the manually movable structure 35 to the plurality of fingers 55 while accommodating the selected sequential movement 95 in proceeding from the stowed state 65 to the open state 70 and reversing the sequential movement 95 in proceeding from the open state 70 to the stowed state 65, all as best shown in FIGS. 11 through 17, with a schematic representation in FIG. 18. Essentially the alternative embodiment 32 of the examination apparatus replaces the flexible elements 170 of the examination apparatus embodiment 31 with the linkages 210, wherein the fingers 55 operation and structure are the same as previously described. Thus, the sequential movement 105 is built into the linkages 210 pivotal relationship to the moment arms 60, in looking at FIG. 18, and FIGS. 11 through 17, wherein the first finger 56 moves 151 initially prior to the second finger 58 moving 151 to allow for the stowed state 65 of the fingers 55 to un-nest 75 and proceed to the open state 70 and following in reverse the second finger 58 has movement 151 prior toward the stowed state 65 before the first finger 56 movement 151 toward the stowed state 65 to allow for the re-nesting relationship 75.

Focusing in particular on FIG. 18 for the examination apparatus 32 alternative embodiment the assemblage 205 is shown schematically for moving the fingers 55 further includes the plurality of linkages 210 each being constructed a substantially rigid extension 220 that is adjacent 225 to a pivotal moment arm 60 of each of the plurality of fingers 55, with the extension 220 also being adjacent to a movable portion 36 of the structure 35 on an opposing end 230 of the extension 220. Wherein the assemblage 205 is sized and configured 235 to be operational for at least one of the fingers 55 to have an increasing mechanical advantage facilitated by an effective change in a moment arm length 61 of the pivotal moment arm 60 in proceeding from the stowed state 65 to the open state 70. Wherein the increasing mechanical advantage is between the manually movable structure 35 and the plurality of fingers 55 that is operational to increase an opening force 150 on at least one of the plurality of fingers 55 from the stowed state 65 to the open state 70 for a fixed substantially constant manual force 155 on the structure 35 in proceeding from the stowed state 65 to the open state 70. In looking closely at FIG. 18, the dynamic moment arm 61 increase can be seen at the increasing mechanical advantage 145 from the extension 220 adjacent position 225 on the moment arm 60 in going from the solid line position to the dashed line position, i.e. from the stowed state 65 to the open state 70. This increasing mechanical advantage would apply to both the first finger 56 and the second finger 58, as both are shown in FIG. 18. Thus, the increased moment arm for increasing mechanical advantage 145 results in a greater force 150 available for the finger 55 from a substantially constant force 155 as manually applied to the structure 35 by the service provider 250, to accommodate a high cavity 245 resistance as against the finger 55 as the finger 55 approaches the full open state 70.

Typically the linkages 210 are preferably rigid extensions 220 for strength, flexibility, light weight, and the ability to be autoclaved, the preferred materials of construction are stainless steel. Alternative materials would include composites, polymers, or any other material that meets the needs for strength as against the manual substantially constant force 155 and autoclavable.

METHOD OF USE

Referring in particular to FIGS. 19 through 26, shown is the typical use of the examination apparatus 30, 31, or 32. As previously alluded to, the stowed state 65 with the fingers 55 nested 75 allows for the streamlined finger 55 leading edge profile 85 to help promote the ease of multiple finger 55 insertion into the cavity 245 by the service provider 250 by preferably grasping the structure 35 as best shown in FIGS. 19, 20, 23, and 24. Once inserted the examination apparatus 30, 31, or 32 can have the fingers 55 proceed to the open state 70 by the service provider 250 applying substantially constant manual force 155 for the first movement 40 selectively to expand the cavity 245 of the creature or patient 240, as best shown in FIGS. 21, 22, 25, and 26. The field of view 260 facilitates the service provider 250 performing observations, doing various procedures, and the like, and as shown in FIGS. 22 and 26, the service provider 250 utilizing optional accessories such as the fluid communication and/or light communication as shown in FIG. 17. Further, an optional retainer element 255, as shown in FIGS. 20 and 24, can be used to help secure the examination apparatus 30, 31, or 32 to the creature or patent 240 in potential situations wherein the service provider 250 would find it difficult to maintain a firm grasp on the structure 35, due to other tasks being performed.

CONCLUSION

Accordingly, the present invention of an examination apparatus 30, 31, or 32 has been described with some degree of particularity directed to the embodiment(s) of the present invention. It should be appreciated, though; that the present invention is defined by the following claims construed in light of the prior art so modifications or changes may be made to the exemplary embodiment(s) of the present invention without departing from the inventive concepts contained therein.

The invention claimed is:

1. An examination apparatus, comprising:
   (a) manually movable structure having a first selective movement from a free state to a compressed state and a second selective movement, being a return movement from said compressed state to said free state;
   (b) a plurality of fingers disposed adjacent to said structure, said fingers having a stowed state and an open state, said stowed state having a nested relationship between said fingers to reduce a silhouette of a leading edge profile of said plurality of fingers in said stowed state, said open state requiring a sequential movement of a first finger prior to a movement of a second finger to proceed from said nested relationship to said open state;
   (c) a means for urging said second finger into said stowed state; and
   (d) a mechanism for moving said plurality of fingers utilizing said structure, wherein said fingers are moved from said stowed state to said open state, wherein said mechanism includes a plurality of flexible elements that communicate movement from said manually movable structure to said plurality of fingers while accommodating said sequential movement in proceeding from said stowed state to said open state and reversing said sequential movement in proceeding from said open state to said stowed state, said flexible elements each being constructed of a cable that is adjacent to a pivotal moment arm of each of said plurality of fingers, with said cable also being adjacent to a movable portion of said structure on an opposing end of said cable, wherein said mechanism is sized and configured to be operational for at least one of said fingers to have an increasing mechanical advantage facilitated by an effective change in a moment arm dynamic length of said pivotal moment arm in proceeding from said stowed state to said open state, wherein said increasing mechanical advantage is between said manually movable structure and said plurality of fingers that is operational to increase an opening force of at least one of said plurality of fingers from said stowed state to said open state for a fixed manual force on said structure in proceeding from said stowed state to said open state.

2. An examination apparatus according to claim 1 wherein said mechanism for moving said fingers further includes a selectable device to vary said pivotal moment arm for a selected initial moment arm length for any one of said plurality of flexible elements that is adjacent to said pivotal moment arm of each of said plurality of fingers, wherein said selectable device is operational for any one of said fingers to have a selectably increasing mechanical advantage facilitated by a selected change in said selected initial moment arm length, wherein said pivotal moment arm further has said moment arm dynamic length change of said pivotal moment arm in proceeding from said stowed state to said open state, wherein said increasing mechanical advantage is between said manually movable structure and said plurality of fingers that is operational to selectably increase an initial opening force of one of said plurality of fingers from said stowed state and further allowing for a selectable increase in said opening force in going from said stowed state to said open state for said fixed manual force on said structure in proceeding from said stowed state to said open state.

3. An examination apparatus, comprising:
   (a) manually movable structure having a first selective movement from a free state to a compressed state and a second selective movement, being a return movement from said compressed state to said free state;
   (b) a plurality of fingers disposed adjacent to said structure, said fingers having a stowed state and an open state, said stowed state having a nested relationship between said fingers to reduce a silhouette of a leading edge profile of said plurality of fingers in said stowed state, said open state requiring a sequential movement of a first finger prior to a movement of a second finger to proceed from said nested relationship to said open state;
   (c) a means for urging said second finger into said stowed state; and
   (d) an assemblage for moving said plurality of fingers from said stowed state to said open state, wherein said assemblage includes a plurality of linkages that communicate movement from said manually movable structure to said plurality of fingers while accommodating said sequential movement in proceeding from said stowed state to said open state and reversing said sequential movement in proceeding from said open state to said stowed state, said plurality of linkages each being constructed of a substantially rigid extension that is adjacent to a pivotal moment arm of each of said plurality of fingers, with said extension also being adjacent to a movable portion of said structure on an opposing end of said extension, wherein said assemblage is sized and configured to be operational for at least one of said fingers to have an increasing mechanical advantage facilitated by an effective change in a moment arm length of said pivotal moment arm in proceeding from said stowed state to said open state, wherein said increasing mechanical advantage is between said manually movable structure and said plurality of fingers that is operational to increase an opening force on at least one of said plurality of fingers from said stowed state to said open state for a fixed manual force on said structure in proceeding from said stowed state to said open state.

* * * * *